(12) United States Patent
Wilkins

(10) Patent No.: US 8,652,311 B1
(45) Date of Patent: Feb. 18, 2014

(54) METHOD AND APPARATUS FOR THE DETECTION OF PATHOGENS, PARASITES, TOXINS AND DESIRED CHEMICAL COMPOUNDS

(76) Inventor: Ebtisam Wilkins, Albuquerque, NM (US)

( * ) Notice: Subject to any disclaimer, the term of this patent is extended or adjusted under 35 U.S.C. 154(b) by 0 days.

(21) Appl. No.: 13/065,926

(22) Filed: Apr. 1, 2011

Related U.S. Application Data

(63) Continuation-in-part of application No. 11/537,915, filed on Oct. 2, 2006, now Pat. No. 7,931,788.

(51) Int. Cl.
*G01N 27/327* (2006.01)

(52) U.S. Cl.
USPC ............. 204/403.01; 204/403.02; 204/403.03

(58) Field of Classification Search
USPC ................. 204/403.01, 403.02, 409–412; 205/777.5, 778, 792
See application file for complete search history.

(56) References Cited

U.S. PATENT DOCUMENTS

| | | | |
|---|---|---|---|
| 4,297,590 A * | 10/1981 | Vail | 307/43 |
| 4,813,424 A | 3/1989 | Wilkins | |
| 4,859,419 A * | 8/1989 | Marks et al. | 422/417 |
| 4,986,271 A | 1/1991 | Wilkins | |
| 5,431,160 A | 7/1995 | Wilkins | |
| 5,476,776 A | 12/1995 | Wilkins | |
| 5,639,428 A * | 6/1997 | Cottingham | 422/112 |
| 6,180,335 B1 | 1/2001 | Wilkins et al. | |
| 7,327,002 B2 * | 2/2008 | He | 257/390 |
| 7,931,788 B1 | 4/2011 | Wilkins | |
| 2007/0072169 A1 * | 3/2007 | Peyvan et al. | 435/4 |

FOREIGN PATENT DOCUMENTS

| | | | | |
|---|---|---|---|---|
| GB | 2289339 A * | 11/1995 | | G01N 32/543 |
| JP | 04-102063 A * | 4/1992 | | G01N 27/46 |
| WO | WO 95/29395 A1 * | 11/1995 | | G01N 21/00 |
| WO | WO 96/02001 A1 * | 1/1996 | | G01N 33/543 |

OTHER PUBLICATIONS

Shah et al. Rapid Amperometric Immunoassay for *Escherichia coli* Based on Graphite Coated Nylon Membranes, Electroanalysis, vol. 15 issue 23-24, 2003, pp. 1809-1814.*
Derwent abstract of Fuji et al. JP 04-102063 A, patent published Apr. 3, 1992.*
Ivnitski D., Abdel-Hamid I., Atanasov P., and Wilkins E., "Biosensors for Detection of Pathogenic Bacteria (A Review)". Biosensors and Bioelectronics, 14, 599-624, 1999.
Hurst M. R. and Wilkins E., "Chemical and Biological Warfare: Should Rapid Detection Techniques Be Researched to Dissuade Usage? Review". American Journal of Applied Scien, American Journal of Applied Sciences 2(4): 79-805, 2005.

(Continued)

*Primary Examiner* — Alex Noguerola

(57) ABSTRACT

The present invention is directed to a method and apparatus for an immunoassay technique that uses amperometric measurements to rapidly analyze different pathogenic microorganisms, including bacteria, viruses, toxins, and parasites. A conductive membrane is used to provide support for antibody immobilization and serve as a working electrode. The proposed technique is adaptable for use with different materials so as to form a membrane having a pore size that is suited to the particular application. A compact and simple disposable element can be used. The immunoassay can be automated using microprocessor control so as to reduce the amount of human intervention in sample analysis.

9 Claims, 17 Drawing Sheets

(56) References Cited

OTHER PUBLICATIONS

Vetcha S., Abdel-Hamid I., Atanasov P., Ivnitski D., Wilkins E.,"Portable Immunosensor for the Fast Amperometric Detection of Anti-hantavirus Antibodies", Electroanalysis, 12, No. 13, pp. 1-5.

Wikins E. and Sitdikov R., "Biosensors for Viruses Detection". Chapter 21 in Smart Biosensor Technology. Editor George K Knopf. CRC Press, p. 567-596, 2007.

Sitdikov R., Ivnitski, D., Abdel-hamid, I., and Wikins E., "Detection and Identification of Organophosphorous compounds: As Chemical warfare agents". CRC publications, Taylor, Taylor & Francis Book #13:978 chapt 11, pp. 293-313, 2000.

Cames E., Wilkins E., The development of a new, rapid, amperometric immunosensor for the detection of low concentrations of bacteria. Part I: Design of the detection system, American Journal of Applied Sciences 2 (3):597-606, 2005.

Sitdikov R and Wikins E. "Detection of Para Influenza and Influenza A Viruses Using Flow-Injection Amperometric Immunosensor", Journal of Applied Research, vol. 7, No. 1, 108, 2007.

Sitdikov R, Wikins E, Yates T, Hjelle B.,"Detection of Hantavirus Using a New Miniaturized Biosensor Device" Journal of Applied Research, vol. 7, No. 1, 86-107, 2007.

Wikins E. and Sitdikov R., "Biosensors for Hanta, Influenza A, and Para Influenza Viruses Detection". Chapter 22 in Smart Biosensor Technology. CRC Press, p. 597, 2007.

Wikins E. and Sitdikov R., "Biosensors for Hanta, Influenza A, and Para Influenza Viruses Detection". Chapter 22 in Smart Biosensor Technology. CRC Press, pp.597-616, 2007.

Cames E., Wilkins E., The development of a new, rapid, amperometric immunosensor for the detection of low concentrations of bacteria. Part II: Optimization of the system f, American Journal of Applied Sciences 2 (3):607-613, 2005.

Ghindilis,A.L. , Atanasov P., Wilkins M., and Wilkins E., "Immunosensors: Electrochemical Sensing and Other Engineering Approaches (A Review) ". Biosensors and Bioelectronics, Biosensors & Bioelectronics vol. 13, No. 1 pp. 113-131.

Ghindilis A.L., Krishnan R., Atanasov P., Wilkins E. "Flow-through Amperometric lmmunosensor. Fast sandwich Scheme Immunoassay ". Biosensors &Bioelectronics 12, 415-423, 1997.

Abdel-Hamid I., Ivnitski D., Wilkins E., "Highly sensitive flow-injection immunoassay system for rapid detection of bacteria", Anal. Chim. Acta ,399, 99-108, 1999.

Vetcha S., Wikins E., Yates T., "Detection of Hantavirus Infection in Hemolyzed Mice Blood Using Alkaline Phosphatase Conjugate ", Biosensors and Bioelectronics 17 (2002) 901-909.

Chemburu S., Wilkins E., "Detection of Pathogenic Bacteria using Highly Dispersed Immunoelectrodes", Biosensors & Bioelectronics, 21,491-499,2005.

Shah J., Chemburu S.,., Wilkins E., Abdel-Hamid I, "Rapid Amperometric Immunoassay for *Escherichia coli* Based on Graphite Coated" Electroanalysis, vol. 15, 2003, 1809-1814.

Ivnitski D., Atanasov P., Abdel-Hamid I., Wilkins E., (Review), "Application of electrochemical biosensor for detection of food pathogenic bacteria", Electroanalysis, 12, 317-325 2000.

Vetcha S., Wikins E., Yates T., "Detection of Hantavirus Infection in Hemolyzed Mice Blood Using Alkaline Phosphatase Conjugate ",Biosensor and Bioelectronics, 17, 901-909, 2002.

Vetcha S., Wilkins E., Yates T., Hjelle B., "Rapid and Sensitive Handheld Biosensor for Detection c Antibodies in Wild Mouse Blood Samples Under Field Conditions", Talanta 58 (2002) 517-528.

Ivnitski D., Wilkins E., Tien H.T., Ottova A., "Electrochemical biosensor based on supported planar lipid bilayers for fast detection of pathogenic bacteria ", Electrochemistr, Electrochemistry Coimmunications 2 (2000) 457-460.

Abdel-Hamid I., Atanasov P., Ghindilis,A.L., and Wilkins E.,"Development of a Flow-through Immunoassay System" . Sensors and Actuators-B, 49, 202-210, 1998.

\* cited by examiner

| Properties | Unit | TGP-H-060 | TGP-H-090 | TGP-H-120 | TGP-H-1.0t |
|---|---|---|---|---|---|
| Thickness | mm | 0.19 | 0.28 | 0.37 | 1.00 |
| Bulk Density | g/cm³ | 0.45 | 0.45 | 0.45 | 0.45 |
| Porosity | % | 78 | 78 | 78 | 78 |
| Gas Permeability | mmaq/mm | 27 | 30 | 33 | 30 |
| Electrical Resistivity | | | | | |
| Thru Plane | Ω·cm | 0.08 | 0.08 | 0.08 | 0.07 |
| In Plane | Ω·cm | 0.005 | 0.005 | 0.005 | 0.005 |
| Thermal Conductivity | Cal/cm sec °C | 0.004 | 0.004 | 0.004 | 0.004 |
| Flexural Strength | MPa | 39.2 | 39.2 | 39.2 | 39.2 |
| Flexural Modulus | MPa | 9800 | 9800 | 9800 | 9800 |

Table 1

| Sample | Current (µA) |
|---|---|
| Sample 1 | 2.22 |
| Sample 2 | 2.26 |
| Sample3 | 2.18 |
| Sample 4 | 2.22 |
| Sample 5 | 2.24 |

FIG. 15 (a)

Table 2

| Sample | Current (µA) |
|---|---|
| Sample 1 | 0.38 |
| Sample 2 | 0.38 |
| Sample 3 | 0.36 |
| Sample 4 | 0.36 |
| Sample 5 | 0.36 |

FIG. 15 (b)

Table 3

| Sample, Blood name | New device, microampere | Result of assay | CDC data |
|---|---|---|---|
| Negative (-) | 0.26 | Control | - |
| Weak positive (+) | 0.75 | Control | - |
| MF 1 | 0.18 | (-) | (-) |
| MF 2 | 0.25 | (-) | (-) |
| MF 3 | 0.28 | (-) | (-) |
| MF 4 | 1.70 | (+) | (+) |
| MF 5 | 0.54 | (-) | (-) |
| Samples 6 to 8 are negative for both the device and CDC data | | | |
| MF 9 | 0.21 | (-) | (-) |
| MF 10 | 1.30 | (+) | (+) |
| MF 11 | 0.18 | (-) | (-) |
| MF 15 | 0.41 | (-) | (-) |
| MF 16 | 2.75 | (+) | (+) |
| MF 17 | 0.21 | (-) | (-) |
| Samples 18 to 28 are negative for both the device and CDC data | | | |
| MF 29 | 0.97 | (+) | (+) |
| MF 30 | 0.32 | (-) | (-) |
| MF 32 | 0.26 | (-) | (-) |
| MF 33 | 0.15 | (-) | (-) |
| MF 34 | 0.12 | (-) | (-) |
| MF 35 | 0.28 | (-) | (-) |
| MF 36 | 2.72 | (+) | (+) |
| MF 37 | 0.43 | (-) | (-) |
| Samples 38 to 49 are negative for both the device and CDC data | | | |
| MF 50 | 0.37 | (-) | (-) |
| MF 51 | 2.07 | (+) | (+) |
| MF 52 | 0.34 | (-) | (-) |
| MF 53 | 1.35 | (+) | (+) |
| MF 54 | 1.30 | (+) | (+) |
| MF 55 | 0.29 | (-) | (-) |
| MF 66 | 1.28 | (+) | (+) |
| MF 74 | 0.22 | (-) | (-) |

FIG. 15 (c)

METHOD AND APPARATUS FOR THE DETECTION OF PATHOGENS, PARASITES, TOXINS AND DESIRED CHEMICAL COMPOUNDS

RELATED APPLICATIONS

The present invention is a continuation in part of application Ser. No. 11/537,915 filed Oct. 2, 2006 now U.S. Pat. No. 7,931,788 of Ebtisam Wilkins for a method and apparatus for the detection of pathogens, parasites and toxins and which is now under a notice of allowance

BACKGROUND OF THE INVENTION

Pathogens such as bacteria, parasites, DNA, toxins, and viruses have emerged as public health problems. Worldwide, pathogenic infections are responsible for more deaths than any other cause. At times, the pathogens are opportunistic when our resistance is low due to Acquired Immuno Deficiency Syndrome (AIDS), immunosuppressive drug therapy, anticancer treatment or other related factors. Food borne disease outbreaks, emergence of newer strains of drug-resistant bacterial pathogens without any forewarning (such as the recent outbreak of Severe Acute Respiratory Syndrome (SARS) in Asia), Bird Flu, or pathogens used as a potentially viable source of biological warfare weapons for mass destruction, necessitate the development of a rapid, portable, analytical unit as an early warning system for real-time detection of bacterial pathogens in field conditions.

U.S. Pat. No. 6,180,335 discloses a flow-through assembly for the detection of bacterial contamination in the food processing industry. The content of U.S. Pat. No. 6,180,335 is incorporated by reference herein. The disposable element disclosed in the patent includes an immunosorbent layer having antibodies to a target microbe affixed thereto, a membrane or carbon powder in support of the immunosorbent layer, and three electrodes for detecting electrochemical signals. The disposable element may be used to measure the level of microbiological contamination in a solid sample caused by a predetermined microbe. This disposable sensor element cannot be used as a commercial product. However, the U.S. Pat. No. 6,180,335 Patent is directed to the detection of food contaminations. The disposable element disclosed therein contains a pre-filter, three ports, and at least one electrode, all of which increase the size of the disposable element and add unnecessary Costs to the assay. Further, in the patent, the filtration membrane used in support of the immunosorbent layer is not conductive, necessitating the presence of an electrode in close proximity to the membrane in order to accurately measure the changes in electron transfer.

The bulky sensor element as shown in FIG. 1 of U.S. Pat. No. 6,180,335 needs continuous replenishment of Ag/AgCl electrode and chlorinization. Also the carbon working electrodes must be cleaned. Therefore a disposable element needs to be developed, designed, and tested. For commercialization we need a disposable sensor with Antigen or Antibodies immobilized so any analytes could be readily tested.

SUMMARY OF THE INVENTION

This application describes a rapid, portable, analytical unit which can be used as an early warning system for real-time detection of bacterial pathogens in field conditions.

Advantages of the technology described herein include decreased analysis time, increased sensitivity, simplification and automation of the measuring procedure, which produces quantitative results, decreased cost, and portability which allows use under non-laboratory and field conditions. The technologies provide results in about 20 minutes, a requirement of only five to ten percent of the time of most current test procedures. A single channel functional prototype unit has been thoroughly tested and used in the experimentation with various analytes. Conceptual designs have been completed for other configurations (including a multi-channel, multi-analyte unit) to address a variety of applications. The portability and speed revealed in the tests will provide substantial advantages over current practices in these markets. The seriousness of food poisoning alone is exemplified by frequent exposure in the popular press.

The standardized, automated immunosensor diagnostic process, when combined with the system's reduced size, will permit trained technicians, rather than scientific specialists, to use it onsite as well as in a laboratory setting. The technology has been developed for a number of analytes including IgG, IgM, $E.\ Coli$ O157R7, total $E.\ Coli$, $Staphylococcus$ sp and Hantavirus. Tests for $Salmonella$ and Hepatitis are in process.

The technology provides a general methodology for fast, sensitive, inexpensive and portable immunoassays over a wide range of analytes such as bacteria, viruses and chemicals. Since this technology offers a faster and cheaper method of employing test procedures that are already approved, regulatory issues are dramatically reduced. Additionally, current conventional immunoassay techniques are comparatively lengthy analyses that usually take several hours.

The immunosensor improves upon conventional immunoassay techniques by the enhancement of immunointeraction efficiency; this is accomplished by using a flow-injection assay technique, which employs immunocolumns. This provides a high area-to-volume ratio of solid-to-liquid phase and leads to a high rate of immunointeraction due to reduced diffusion limitations. Another area of improvement is the development of a faster and more sensitive detection method using electrochemical detection of the labeled immunospecies.

The potential applications of this novel immunoassay are based upon its advantages relative to existing techniques, namely:
 1) It is 15 to 20 times faster
 2) It is a highly-automated assay that can be conducted by less-trained personnel
 3) It can be configured as a portable unit, which allows assays to be conducted in the field.

The technology is based on a "sandwich" scheme, which is more sensitive than the usual "displacement" scheme. It is especially effective for large molecular weight analytes, which represent the vast majority of applications in the target industries.

The present invention is directed to an immunoassay unit and a disposable sensing element that uses amperometric measurements to rapidly detect and analyze different pathogenic microorganisms, including bacteria and viruses, DNA and parasites. In accordance with one aspect of the present invention, at least one conductive membrane and/or the immunosorbent powder is used to provide support for antibody immobilization and serve as a working electrode, or it could be used by itself without being a working electrode. This conductive membrane can be fabricated of a conductive material or can be a nonconductive material over which a conductive material is coated.

In either case, the proposed technique is adaptable for use with different materials such as carbon powder or so as to form a membrane having a pore size that is suited to the particular application. Another aspect of the present invention relates to a compact and simple disposable element that can be easily assembled and disassembled. In still another aspect of the present invention, the immunoassay is now automated using microprocessor control so as to reduce the amount of human intervention in sample analysis.

In summary, this broad-based technology was developed using a "sandwich-scheme" immunocolumn with enzymatic labeling and amperometric signals. It has been incorporated in a semi automated, portable, functional prototype which provides for highly-sensitive, quantitative detection of levels of most large molecules in a sample. In addition to detecting pathogenic infections, applications are numerous in such fields as medical and veterinary diagnostics, food processing quality control, epidemiology field analysis, and environmental chemical analyses. Anticipated products include a variety of automated units with substantial competitive advantages and a series of disposable flow-through immunocolumns specific to each analyte to be diagnosed. Proprietary cartridges of commercially available immunochemicals will be part of the automated process.

BRIEF DESCRIPTION OF THE DRAWINGS

FIG. 15 (a) Table 1 shows the response of the system using the two conjugates peroxidase labeled and alkaline phosphatase labeled anti-rabbit IgG.

FIG. 15 (b) Table 2 shows the response for Rabbit IgG as analyte and peroxidase labeled anti-rabbit IgG as the conjugate.

FIG. 15 (c) Table 3 Deer mice blind blood samples and CDC data were given us form Dr. Terry Yates (Museum of Southwestern Biology, Department of Biology, University of New Mexico).

DETAILED DESCRIPTION OF THE INVENTION

One aspect of the present invention relates to the use of conductive powder or membrane in an immunoassay, which acts both as a solid phase support for antibody immobilization and or also as a working electrode. Since the immuno-interactions and amperometric measurement occur at the same sites, a significant increase in the magnitude of the electrochemical response is resulted.

In one embodiment, non-conductive membrane such nylon membrane is coated with a conductive material, such as graphite powder. Graphite can be deposited onto membranes in different ways, including, but not limited to, dip coating, spin coating, and vapor coating. In operation, graphite power is first mixed with a suitable solution to form slurry. In one preferred embodiment, cellulose acetate dissolved in acetone is used. Subsequently, a piece of nylon membrane can be dipped into the slurry for coating. As an alternative a spin coater, such as the one with model no. EC 101 manufactured by Headway research Inc, Garland, Tex., can be used to coat the membrane. The coated membranes are then dried at room temperature before use.

Figure 1:
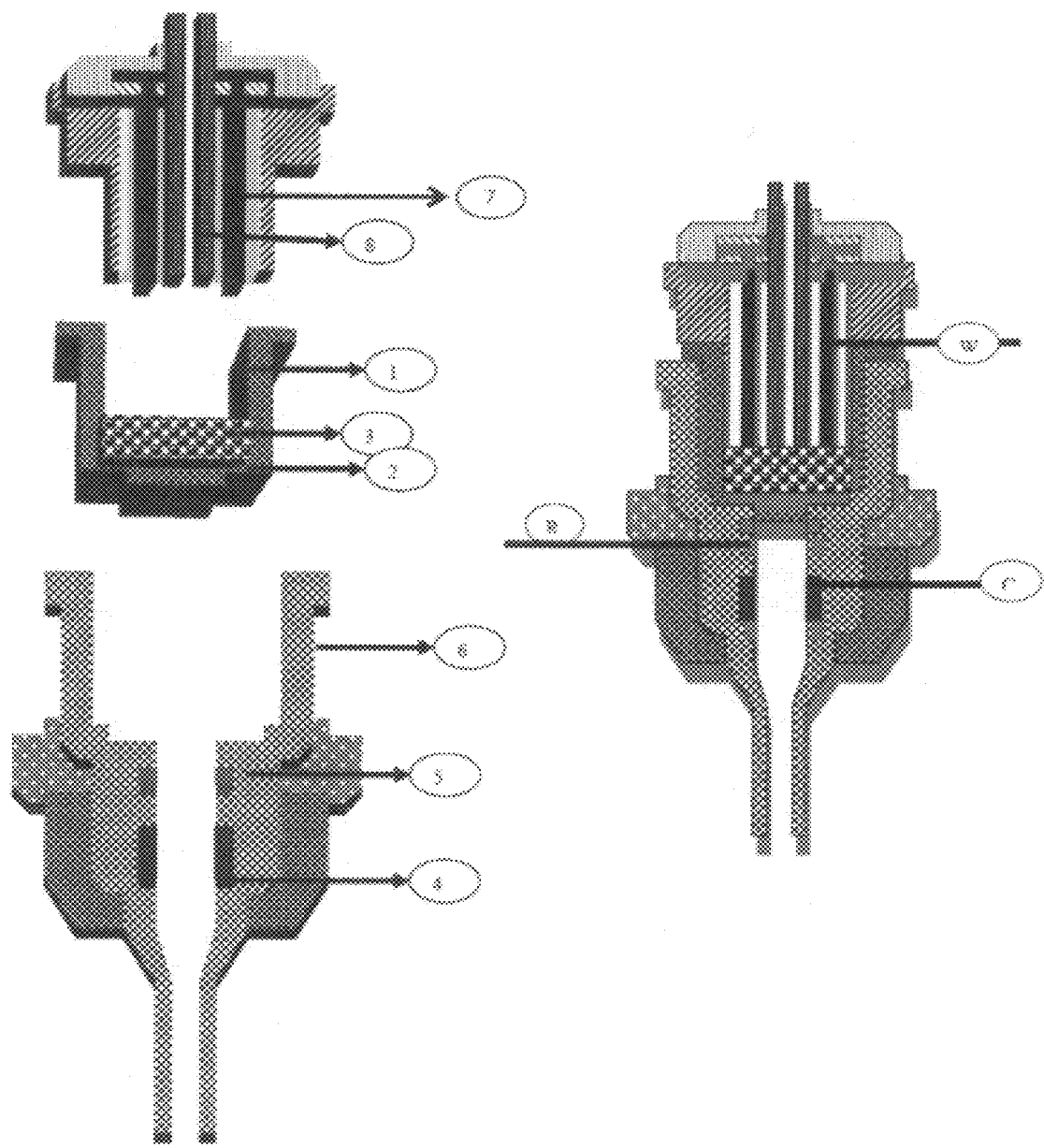
FIG. 1 is a schematic of the flow through immunosensor assembly (1) immunocolumn (2) filtration membrane (3) layer of carbon deposited on top of the membrane (4) counter electrode (5) reference electrode (6) glass capillary and (7) current collectors (8) working electrode.
Figure 2:
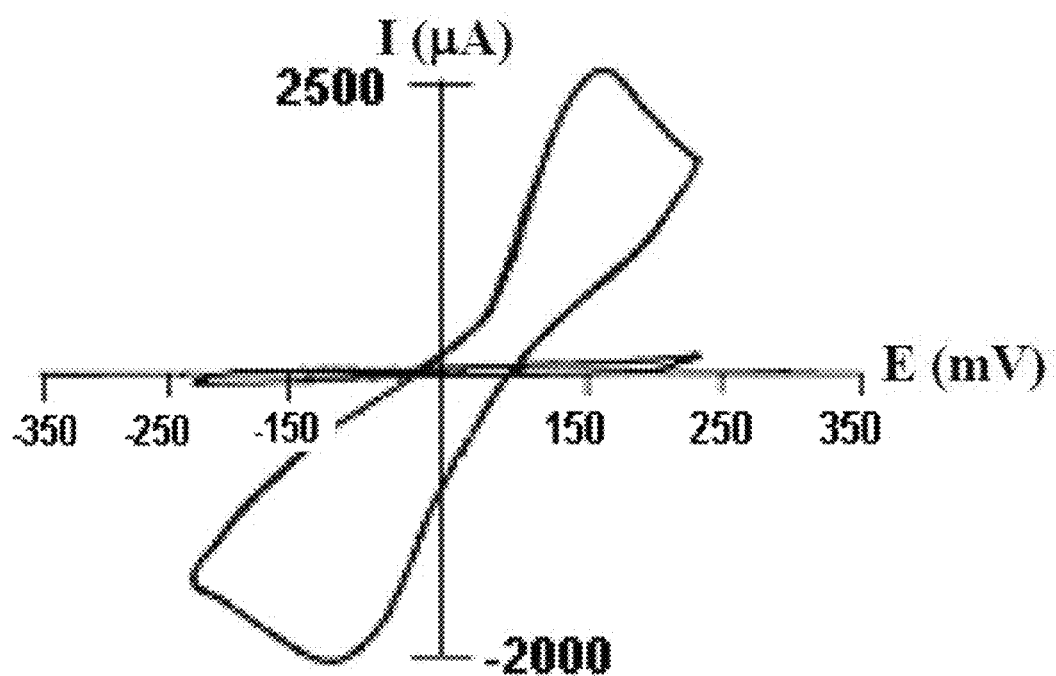
FIG. 2(a) is a Cyclic Voltammograms of a dip-coated nylon membrane. Conditions: scan rate of 20 mv/sec; iodine concentration of $1\times10^{-4}$, 20 mM phosphate buffer (pH 5.
FIG. 2(b) is a Cyclic Voltammograms of a spin-coated nylon membrane. Conditions: scan rate of 20 mv/sec; iodine concentration of $1\times10^{-4}$, 20 mM phosphate buffer (pH 5.8).

Membranes prepared by different coating methods may possess different characteristics. For example, the spin-coating technique produced a well controlled, thin, and evenly distributed graphite layer, as shown by the SEM photographs. On the other hand, graphite layers formed by dip-coating technique were less controlled and thicker. See FIG. 2. Further, when using the same nylon membrane and graphite slurry, the pores size produced by spin coating is smaller than that produced by dip-coating.

Figure 2A:
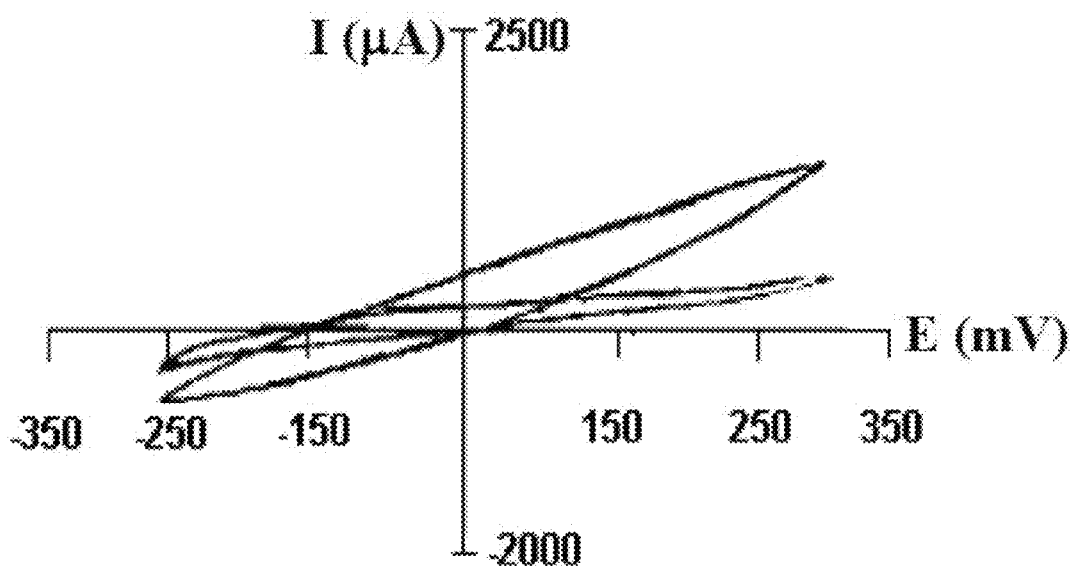
Figure 2B:
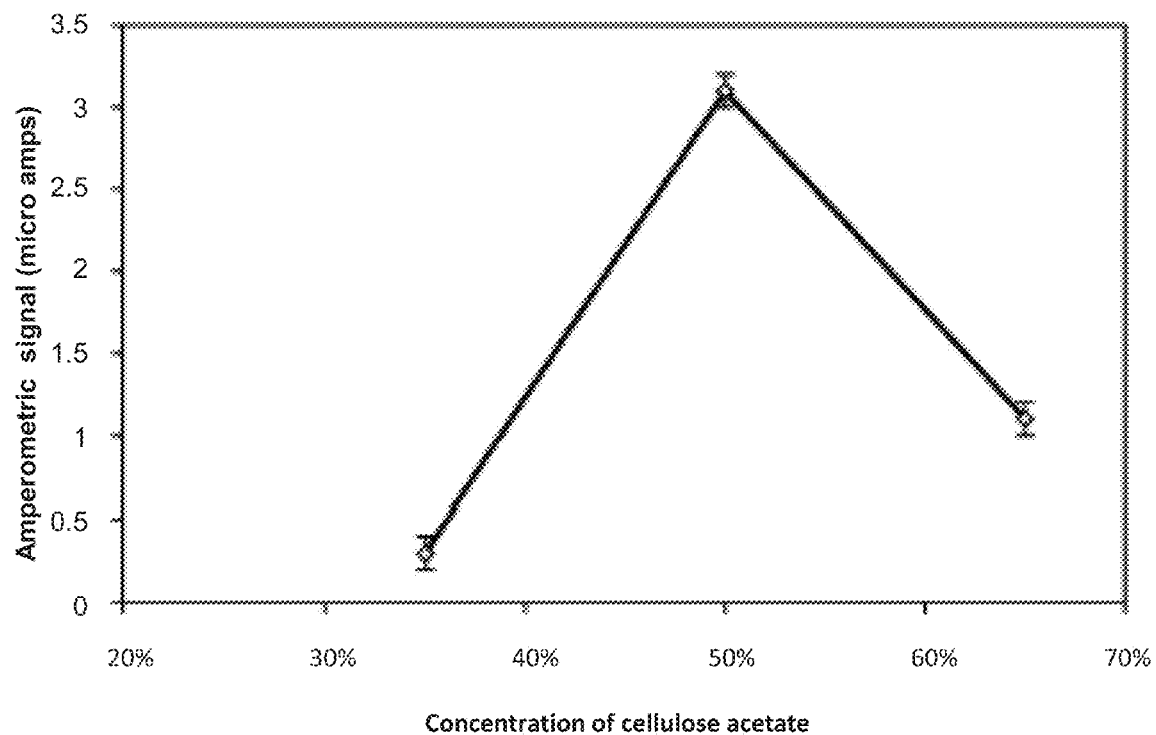
Figure 3A:
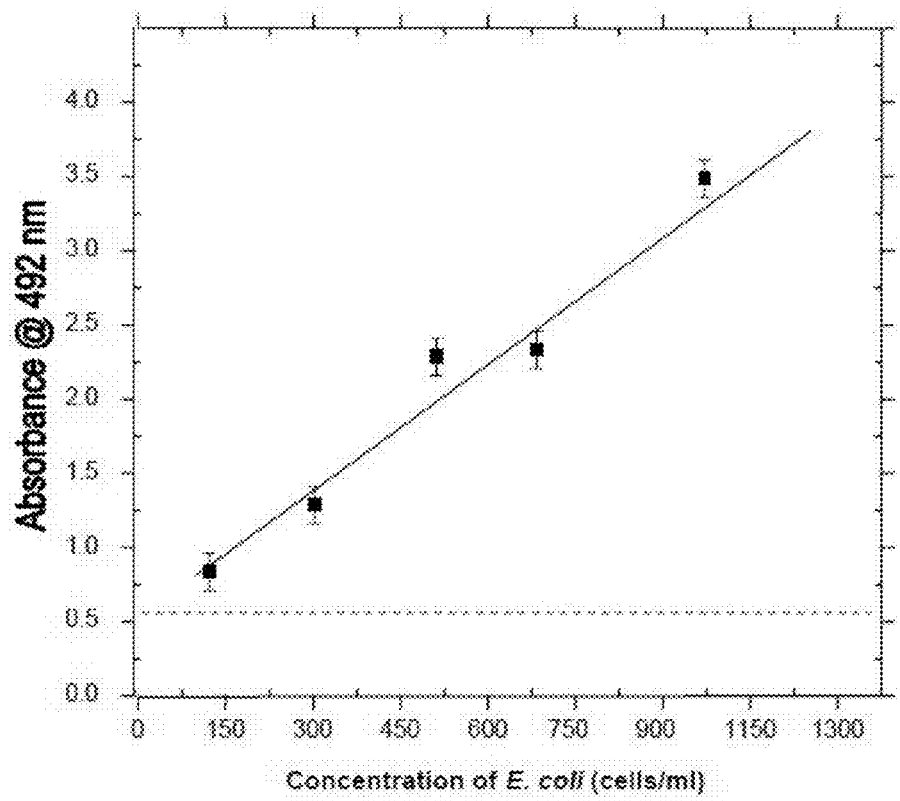
FIG. 3 (a) Calibration curves for amprometric detection of total E. coli. The lowest detectable concentration is 50 cells/ml at a flow rate of 100 µl/min. All measurements were done in triplicate (n=3) and data points are presented as mean±S.D. (b) Calibration curves for amprometric detection of L. monocytogenes. The lowest detection concentration is 10 cells/ml at a flow rate of 100 µl/min. All measurements were done in triplicate (n=3) and data points are presented as mean±S.D. (c) Calibration curves for amprometric detection of C. Jejuni. The lowest detection concentration is 50 cells/ml at a flow rate of 100 measurements were done in triplicate (n=3) and data points are presented as mean±S.D. Background is indicated by dashed line
Figure 3B:
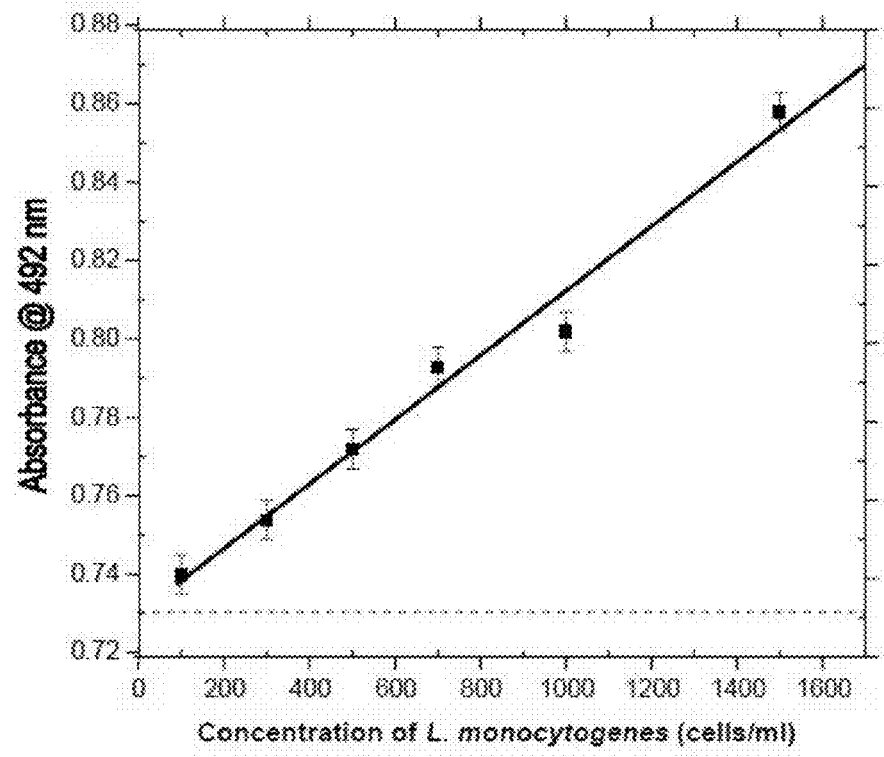
Figure 3C:
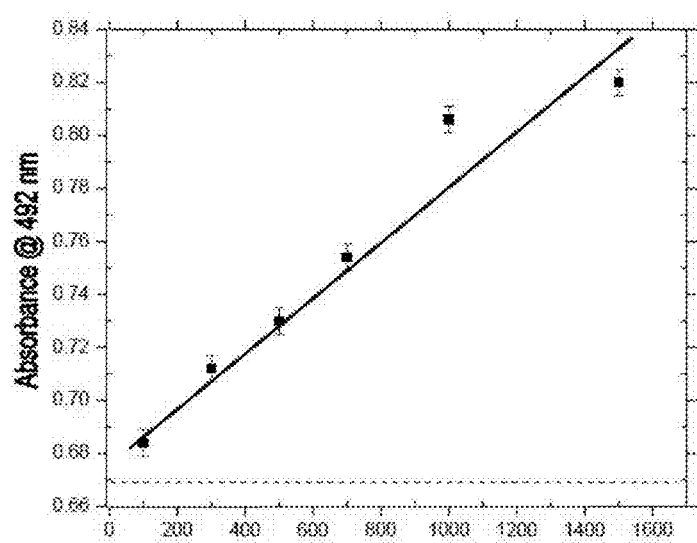

However, dip-coated membranes exhibit better electrochemical properties when compared with spin-coated membranes, as shown in FIGS. 2a and 2b by cyclic voltammetry. Specifically, iodine reduction peaks were more pronounced in the dip-coated membranes (FIG. 3). Furthermore, the difference in current magnitude between the CV in absence and presence of iodine was much greater in the case of dip-coated membranes. This may be attributed to the higher surface areas of graphite that is available, as shown from the SEM photographs.

Figure 4:
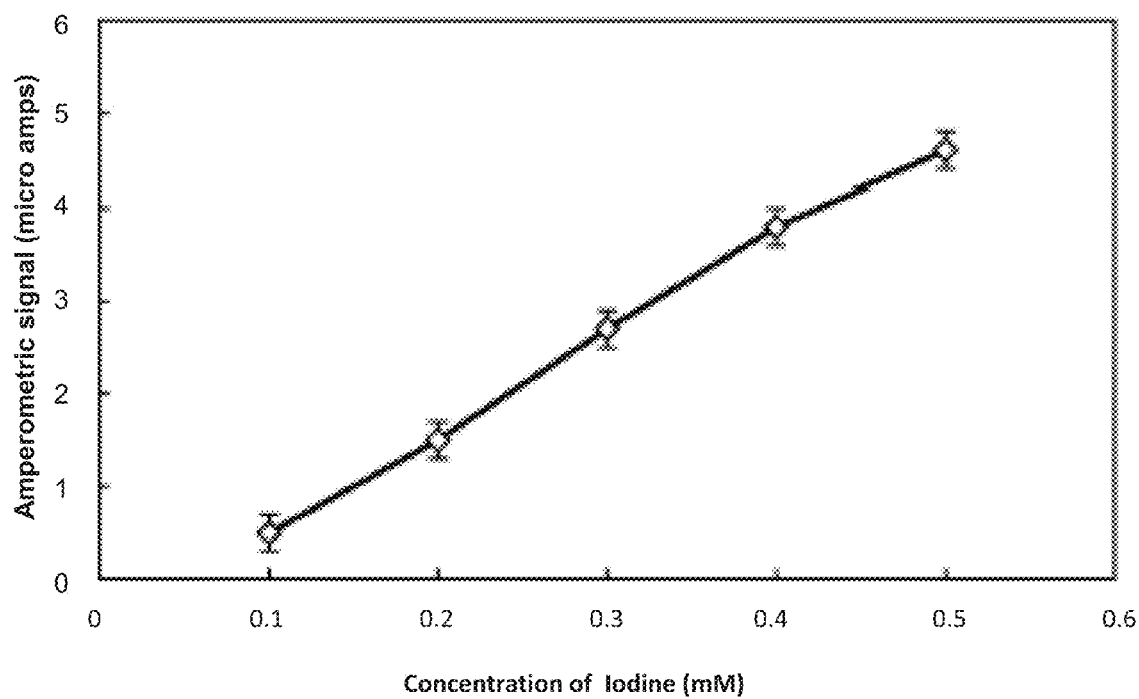
FIG. 4 shows the effect of graphite layer thickness on the amperometric signal resulting from iodine reduction. Thus, in a preferred embodiment, membranes thickness is the range of 450 µm.

The thickness of the graphite film formed on the nylon membrane can be controlled by how many times the membrane is dipped into the slurry or, in the case of a spin coating, the speed and duration of the spin. It has been observed that increased thickness in a certain range may cause an increase in amperometric signal due to the increased electro-active area. However, further increase in graphite layer thickness may result in a decreased amperometric signal because of the appearance of cracks in the graphite layer, which in turn may cause electrical discontinuity and hence a smaller surface area as shown in FIG. 4.

The choice of a suitable membrane pore sizes is crucial for achieving high sensitivity. This is because membranes with too small pores may cause the deposition of carbon/graphite might cause partial blockage of the membrane pores, and consequently a nonspecific, physical entrapment of pathogen as well as increased flow resistance. On the other hand, membrane with too big pores may result in a great portion of the immunoassay solution to flow through the membrane without having enough contacts of the immunosorbents. Consequently, nylon membranes with different pore sizes have been tested and it appears that nylon membrane having a pore-size of 5 μm provides an optimal result for graphite deposition, allowing the formation of a conductive layer while still maintaining adequate flow properties.

The solution used to mix with graphite powder to form slurry may also affect the electrochemical properties of the membrane. Specifically, it has been observed that the ratio of cellulose acetate to acetone is important. As shown in FIG. 6, the amperometric signal is low for both high and low concentrations of cellulose acetate. This might be because that a high concentration of cellulose acetate (65% v/v in acetone) results in a highly viscous membrane that clumps and cracks upon drying while a very low concentrations of cellulose acetate (35% v/v in acetone) results in a highly fluid composition that is difficult to cast evenly over the nylon membrane. Thus, as a preferred embodiment, a cellulose acetate concentration of 50% v/v in acetone can be used to produce a membrane with acceptable amperometric response and ease of casting.

Figure 7:
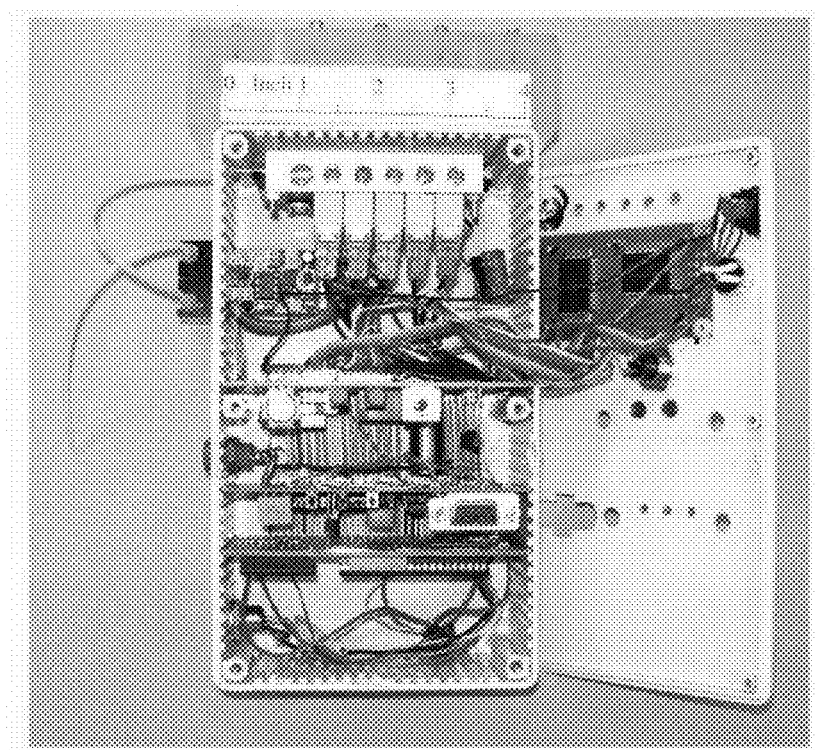
FIG. 7 is a photo of portable automated immunosensor unit.
Figure 8:
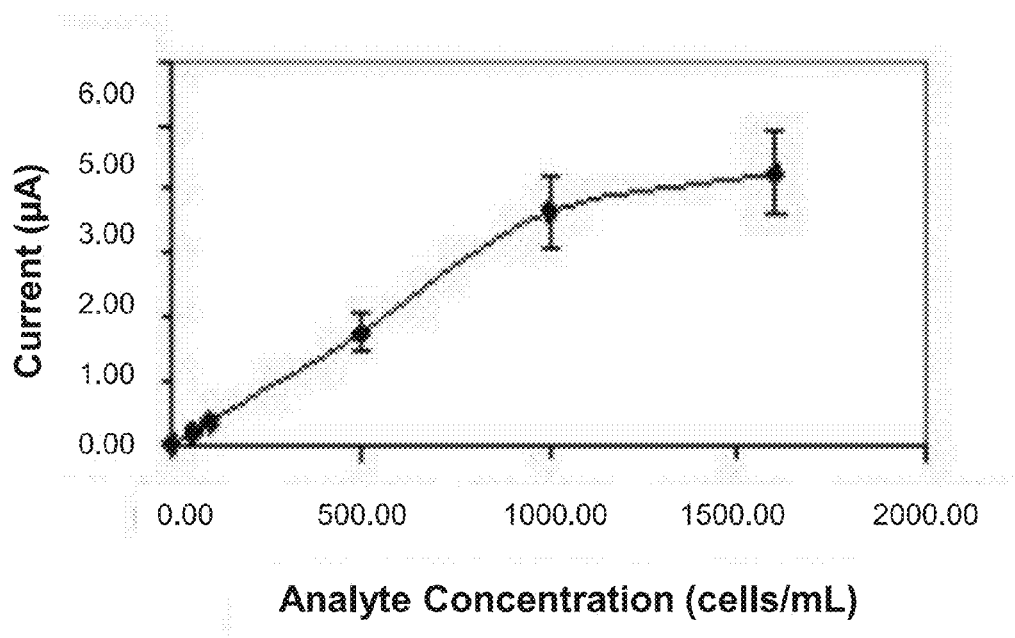
FIG. 8 shows the calibration curve for E. coli using optimized immunoassay procedure showing linear dependence on concentration over working range (50-1000 cells/ml).
Figure 9:
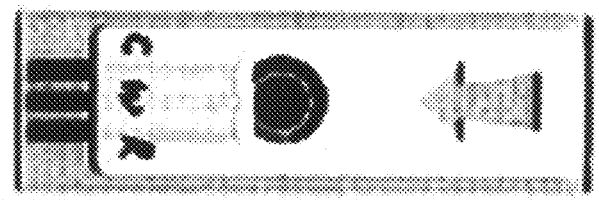
FIG. 9 shows a screen-printed commercially available disposable sensor element.

The graphite-coated membranes can be further processed for immobilizing the desired antigen or antibody by well-established method in the art, such as the use of Woodward's Reagent K. The present invention should not be limited to the one embodiment wherein nylon membranes were coated with graphite powders. Other types of porous membranes recognized in the art, such as carbon fiber paper, polycarbonate membrane, etc., may also be used as the underlying membrane for coating. The coating material used in the present invention can be any conductive material that is capable of being deposited on porous membranes, including, but not limited to, graphite/carbon, conductive polymer, etc. Further, the subjects that can be immobilized on the resulted conductive membrane can be either antibodies or antigens. Even further, the conductive membrane can be used in a reaction chamber as shown in FIG. 7 or in a flow-through immunoassay unit as disclosed previously or in the present invention below.

Another aspect of the current invention relates to the use of a conductive membrane, such as the carbon paper manufactured by Toray Industries, Inc., Tokyo, Japan, directly in an immunoassay without coating. Because of the immunosorbent and conductive nature of the conductive membrane, it served both as a support for immobilizing immunoagents and, at the same time, as an electrode for electrochemical measuring.

Figure 5:
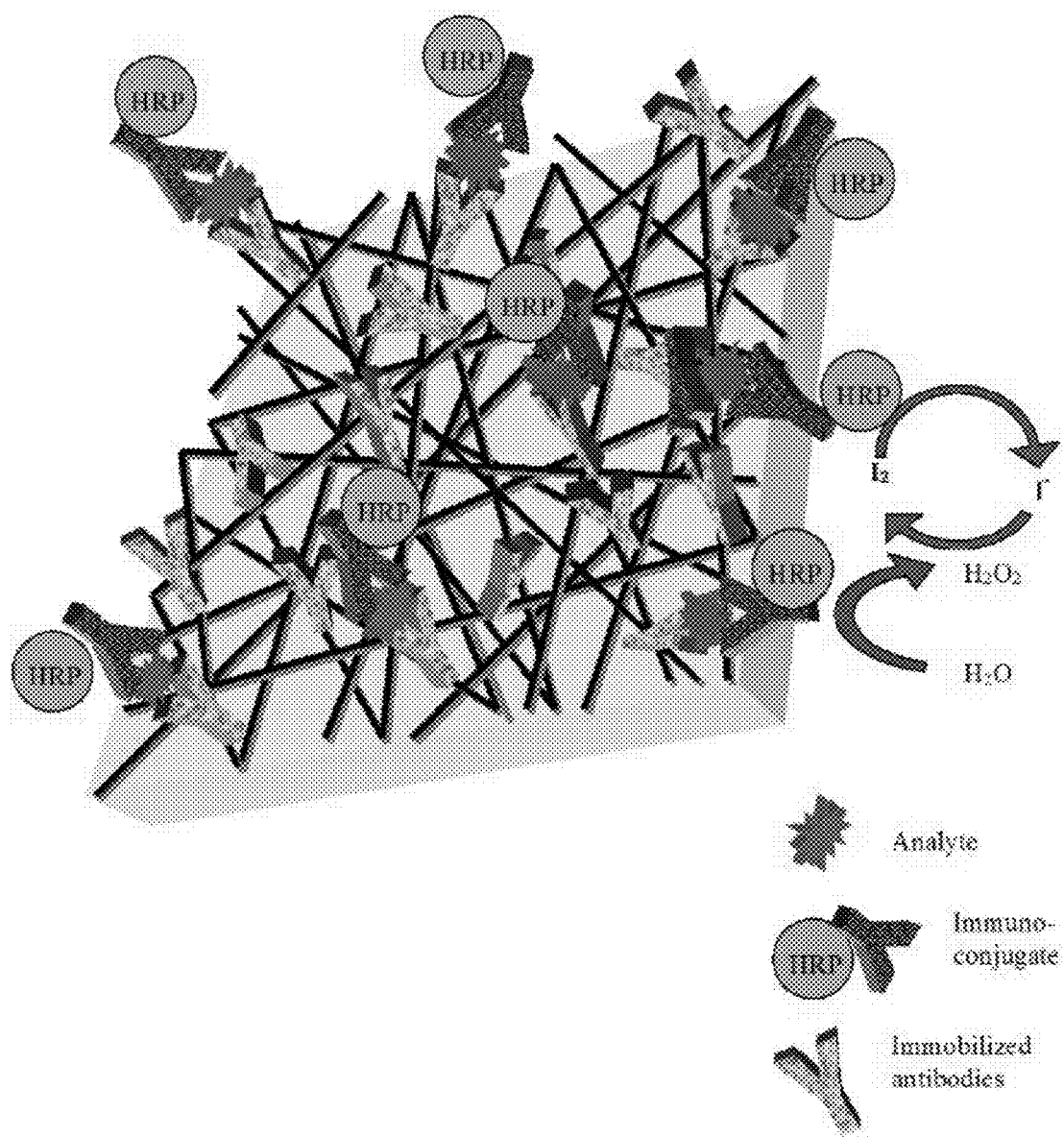
FIG. 5 is a representation of immunofilteration membrane made from Toray carbon paper with determined by an Atomic Force Microscope.
Figures 6A, 6B:
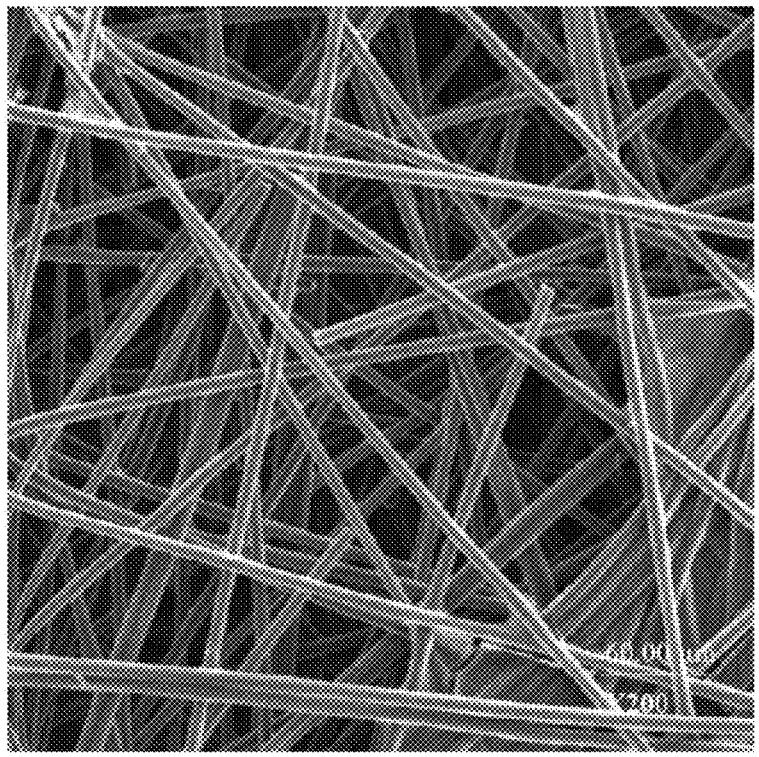
FIG. 6a is an SEM microphotograph of the carbon paper.
FIG. 6b contains physical data for a variety of different paper thicknesses, provided by the manufacturer.

A design based on the use of Toray carbon paper as the solid support for the immunofiltration membrane is shown in FIG. 5. In such an instance, the carbon paper offers a large surface area to volume ratio and, at the same time, it could function as an electrode. The carbon paper consists of pores whose size is on the same order of magnitude as some target analytes, making it ideal for filtration. The carbon itself possesses characteristic pores whose size is of the same order as most antibodies, making it also ideal as an immunosorbent. However, there are times when the carbon paper is not completely satisfactory with respect to its pore size or other characteristics. In such cases, the carbon paper can be coated by the coating method disclosed in the current invention. An SEM microphotograph of the carbon paper is shown in FIG. 6a.

The use of conductive membrane such as carbon paper or graphite coated nylon membrane as an immunofiltration membrane has many advantages. For example, the conductive membrane has high tensile strength and high modulus, good handling and flexibility, excellent thickness uniformity, and minimal electrochemical corrosion. Further, the use of conductive membrane eliminates the problems associated with construction of a complex disposable sensing element used in previous heterogeneous flow immunosensors. Disposable sensing elements have previously consisted of plastic columns with membrane filters on which the immunosorbent is deposited by centrifugation in order to form an immunoelectrode to be used in electrochemical detection. This requires extensive preparation in order to create, driving up the cost of the assay and increasing possibilities for error. However, using carbon paper or other coated membranes as an immunofiltration membrane as well as an immunoelectrode would simplify the system, reduce the cost, and meanwhile increase the sensitivity and reliability of the system.

Further, the traditional heterogeneous immunosensor requires the regeneration of the immunosorbent after each assay, a process involves the use of chaiotropic reagents to break the antigen-antibody bond and inevitably results in a loss of enzyme activity increases the cost and complexity of the assay The use of a conductive immunofiltration membrane, either coated or not coated, permits the construction of immunoassay elements that are disposable and inexpensive. This would simplify the assay procedure and reduce its cost and at the same time ensure constant activity of the immobilized immunoagents without the need for regeneration of the support.

Another aspect of the present invention relates to a compact yet low-cost disposable unit for flow-through immunoassay. A disposable conductive membrane for use in conducting an immunoassay comprising: a disposable conductive material or a nonconductive material coated with a conductive material, means for providing a solid phase support for antibody immobilization and means for acting as a working electrode.

Figure 11:
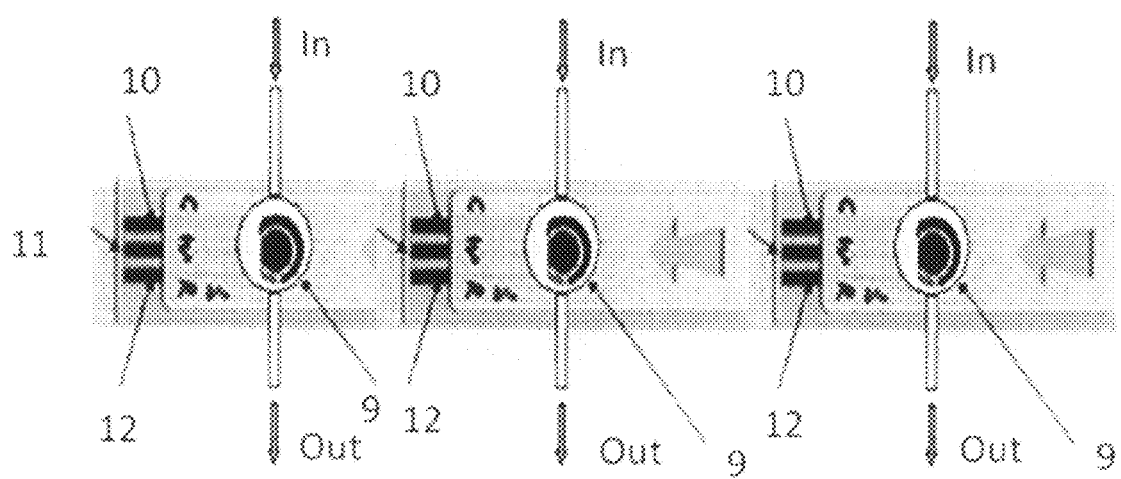
FIG. 11 shows the design of the new multi channel disposable sensing element: 9—flow cell with in and out flow, 10—Carbon counter electrode, 11—Carbon working electrode, 12—Ag/AgCl reference electrode, 5—five-channel injection micro valve manifold.
Figure 17:
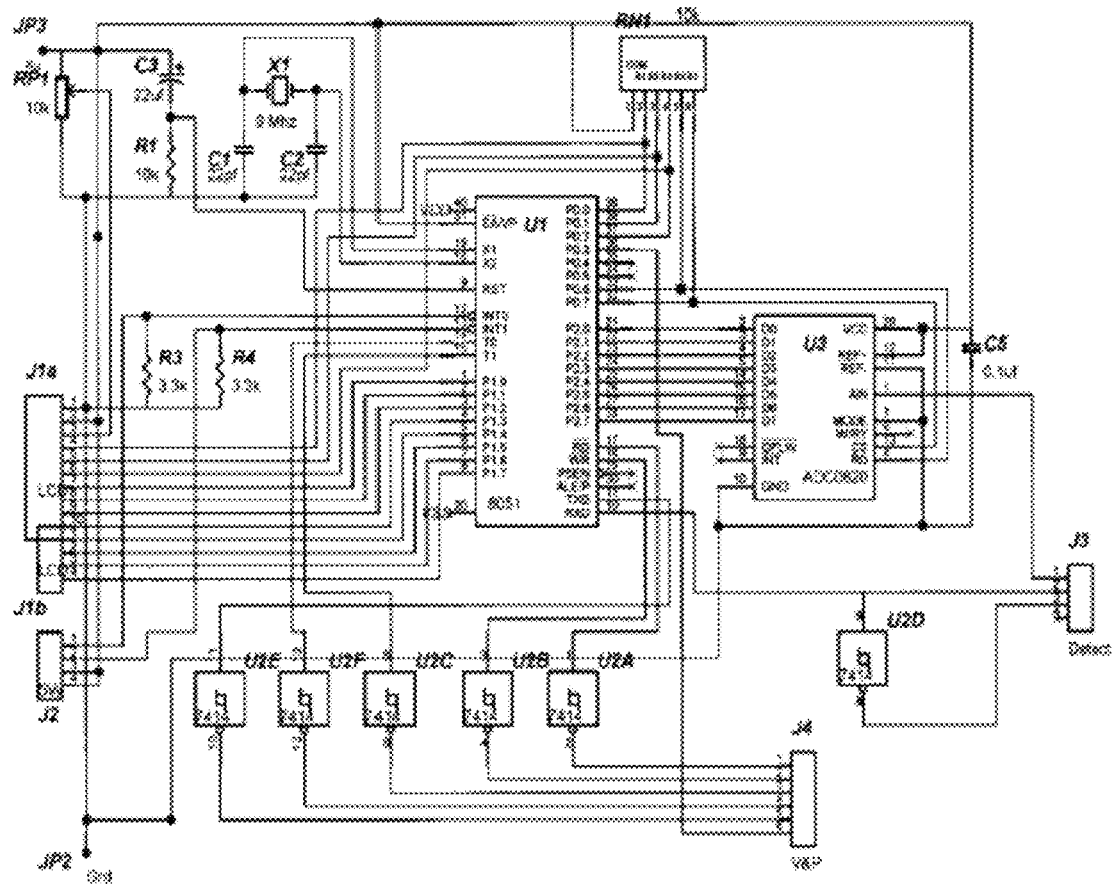
FIG. 17 Wiring Diagram for the Microcontroller.

The focus on development of a disposable sensing element for an automated simple single or more channels on-line flow-injection immunoassay amplification procedure and amperometric biosensor prototype that we have already developed for fast, quantitative detection of low concentrations of total *E. coli, S. Aureus* hantavirus and Influenzas. Qualitative detection of low concentrations of Hantavirus, Influenza A, Bird Flu, and Para influenza. The system will be arranged as a portable unit. The photo of the unit is shown in FIG. 7, all components are easily accessible allowing ease of service and maintenance. Further utilization of amperometric detection in comparison to spectrophotometer allows for the substantial limitation of reagent consumption, eliminates optical elements from the measuring unit. And the use of higher working dilutions of the sample (1:200-1:500) minimizes the interference effects and allows one to ignore the difference in the color and turbidity of natural samples for hanta virus. Our unit was found to be robust in field operations: in terms of accuracy, reproducibility, and ease of use, sensitivity and ability to compensate for interference. The unit exhibits good response stability. The sensitivity of the immunosensor in this preliminary evaluation had no false positive or false negative samples with 100% accuracy using hanta virus rodent blood.

Testing the new circuit with optimization using the old sensor system, the overall assay time was found to be 17 min. This optimized assay could detect the target analyte 50-100 cells/ml, in a linear fashion as shown in FIG. 8. Higher concentration of analyte were analyzed, however, the results were not linear. This indicates that there is a saturation point in the system that is slightly higher than the maximum value of the described working range. To evaluate the immunosensor performance in real samples for use in medical applications, samples of dialysate from patients were evaluated to determine if *E. coli* was present, which could lead to peritonitis. First, sterile dialysate was spiked with known concentrations of bacteria to generate a calibration curve for the sensor, as well as the ELISA, which is shown below in FIG. 8. Next, blind samples that were known to have bacterial contamination were assayed using the newly developed sensor, with the old sensing element and the results were compared to that of a standard ELISA, shown in FIG. 8. It can be seen that the sensor system gives results that are within few percentage points of the standard ELISA values. However, the immunosensor quantified the bacteria in 17 minutes, while preparation and use of the ELISA took two full days. Also, a much smaller volume of immunochemicals can be utilized by the sensor, which can lead to significant cost decrease if many samples are being tested. This means that the sensor can be a good alternative to the ELISA, and has the potential to be used in several similar medical applications.

Engineering of the Disposable Sensing Element

A Disposable Sensing Elements Design, Development and Standardization of.

The disposable sensing elements will be engineered in the form of a one or more channel cartridge as illustrated in FIG. 9 for simultaneous measurement of total *E. coli*, and *S. Aureus*, hanta virus and bird Flu in bio-samples without preenrichment.

The setup with a printed screen disposable element could function with the electric circuit described in FIG. 8. The unit should exhibit good response stability when tested earlier with our bulky sensor element. The sensitivity of the immunosensor was 100% in this preliminary evaluation, with no false positive or false negative samples usinghanta virus rodent blood. We will use a special filter paper and immobilize the antibodies on it. Also we have to build in this proposal a flow cell made out of glass or plastic and fixed over the commercially screen-printed electrode, which is shown in FIG. 10.

The special filter paper with covalent immobilized antibodies will be attached onto the working electrode site of screen-printed electrode, and will play both of roles immunosorbent using this special filter paper or carbon particles as immunosorbent and working electrode simultaneously allows detection of bacteria with high sensitivity and selectivity. The inner volume of the cell is in the range of 55 μL A disposable unit to be used in a flow through immunoassay comprising: an immunosorbent layer having immobilized antibodies that bind to a target analyte in a sample solution; a screen printed electrode having at least one current collector which, a disposable unit can be selected from the group of screen printed, powder or a carbon paper filter; wherein, the screen printed filter or powder is inserted into the disposable unit, and it forms electrical contact with said immunosorbent layer, with a three electrode system; and a holder into which the disposable unit may be inserted with an outlet capable of contacting the solutions during the immunoassay. Filter embodiment where did it come up-in the detailed description. This design of disposable sensing element offers an easy and convenient way to use and commercialize the sensor.

Engineering of the Flow-Injection Enzyme Immunoassay Procedure with the Disposable Sensing Elements Testing of different concentration of Hantavirus, Bird Flu, *E. Coli* and *S. Aureus* modifying the design to confirm our ELISA data. Initial studies will use laboratory cultures of coliform bacteria at known low and high cell concentration. The total number of bacteria in each sample will be known.

Engineering Design of the On-Line Flow-Injection Enzyme Immunoassay Procedure The main characteristics of the portable flow-injection immunoassay procedure (flow rate, incubation time, concentrations of conjugate and substrates, volume of sample, working temperature, configuration and geometric parameters of the flow-through electrochemical sensor) will be investigated in order to increase the sensitivity of the assay, and decrease the time of measurement. constants. FIG. 11 describes the new multi-channel laser engraved sensor element inlet & outlet for the flow of analytes connected to the electronic circuit in FIG. 17 with electronic valves. The disposable element can be designed and manufactured at the Center of High Technology Materials at UNM (CHTM). The flow channels have to be covered with either glass or plastic material. The effect of such factors as the pore size and thickness of membrane, flow rates and temperature on the transport phenomena will be also investigated. An assembly to be used in a flow through immunoassay, comprising: a layer of immunosorbent having immobilized antibodies that bind to a target analyte in a sample solution; a screen printed electrode comprising of at least one current collector which, when the filter or powder is inserted into the disposable unit, forms electrical contact with said immunosorbent layer, with three electrode system; a holder into which the disposable unit may inserted, with inlets which are capable of contacting the solutions during the immunoassay; and a holder with an outlet which goes to disposal.

The main characteristics of the portable flow-injection immunoassay procedure (flow rate, incubation time, concentrations of conjugate and substrates, volume of sample, working temperature, configuration and geometric parameters of the flow-through electrochemical sensor) will be investigated in order to increase the sensitivity of the assay, and decrease the time of measurement. The optimal antibodies for immunosensors will be chosen on the basis of measured kinetic constants. FIG. 11 describes the new multi-channel laser engraved sensor element inlet & outlet for the flow of analytes connected to the electronic circuit in FIG. 17 with electronic valves. The disposable element can be designed and channels for the flow of analytes connected to the electronic circuit in FIG. 7 with electronic valves. The disposable element can be designed and manufactured at the Center of High Technology Materials at UNM (CHTM). The flow channels have to be covered with either glass or plastic material. The effect of such factors as the pore six and thickness of membrane, flow rates and temperature on the transport phenomena will be also be investigated.

Fabrication of One or More Electrochemical Biosensor Prototype

Development of an automated, one or more channel electrochemical biosensor prototype will be used to develop one channel, automated electrochemical biosensor. Additional Channels can be added to the system consists of more channels amperometric disposable sensing element in a rotating cartridge, can be used.

Figure 10:
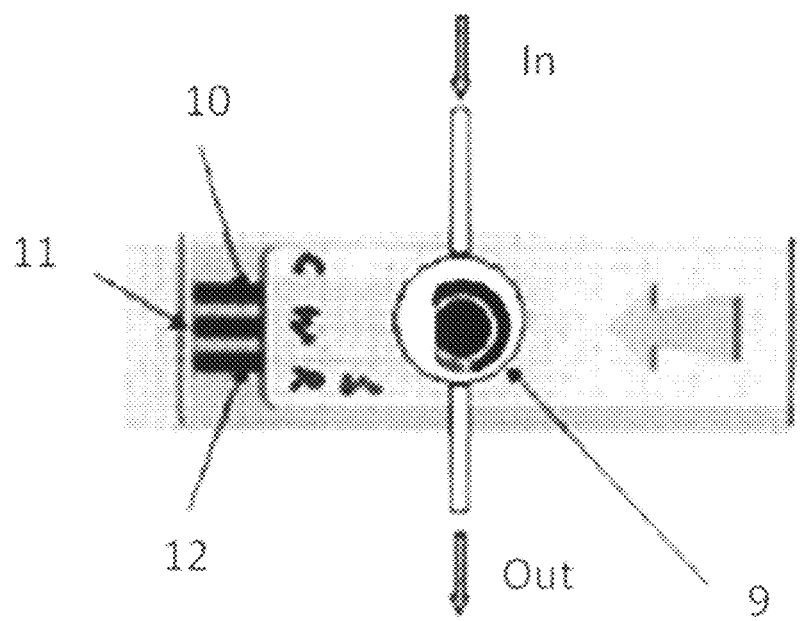
FIG. 10 is the design of the flow-injection cell for the disposable sensing element: 9—flow cell with in and out flow, 10—Carbon counter electrode, 11—Carbon working electrode, 12—Ag/AgCl reference electrode.

Preferably, the disposable multi unit as illustrated in FIG. 11 (disposable element) other shapes may also be used. The disposable unit is preferably made of plastic or glass or other non-conductive materials. The cylindrical or any other shape column is hollow, having an inner capacity surrounded by the cylindrical walls. The cylindrical column or any other shape column further comprises two ends, an upper end and a lower end, with openings at each end. The upper opening is connected to the inlet of different solutions, thus opens the inner capacity of the cylindrical column or any other shape to accept the insertion of an object or tube connection that has a smaller diameter. On the other hand, the solution will fall onto the membrane or filter affixed on the center carbon electrode's (the working electrode) lower opening letting the flow exit the unit after it passes through or over the membrane or the particles and be collected as shown in FIG. 10.

In one embodiment of the present invention, the membrane is placed on the Carbon electrode that is a screen printed or micro fluidics fabricated. This carbon membrane is conductive by itself, such as the carbon paper manufactured by Toray Industries, Inc., Tokyo, Japan. It can be either coated or not coated by a conductive material as described above in the present invention. In another embodiment, the membrane itself is nonconductive, but is coated with a conductive material such as graphite so that the resulted membrane is conductive. In both embodiments, the membranes are capable of being a support for immobilizing immuno-reagents and, at the same time, an electrode.

In yet another embodiment, highly dispersed fine particles of conductive material such as carbon can be used. In such an instance, the membrane functions primarily as a supporting material to prevent the carbon particles from falling through the lower opening of the column. It is immaterial whether the membrane is conductive or not. In a preferred embodiment, highly dispersed carbon particles Ultra Low temperature Isotropic Carbon (ULTI) is used.

A preferred embodiment: The entire assembling process in the previous sensor has been eliminated and now it is simpler and easy to operate. So is the disassembling process after the completion of an experiment. For every new immunoassay, a new disposable unit is used, ensuring both accuracy and efficiency. Further, an array of the disposable unit can be prepared, having different antibodies or antigens immobilized on the surface of the immunosorbents for the detection of a wide range of pathogens, including, but not limited to, bacteria, viruses, parasites, DNA or toxins.

Figure 12:
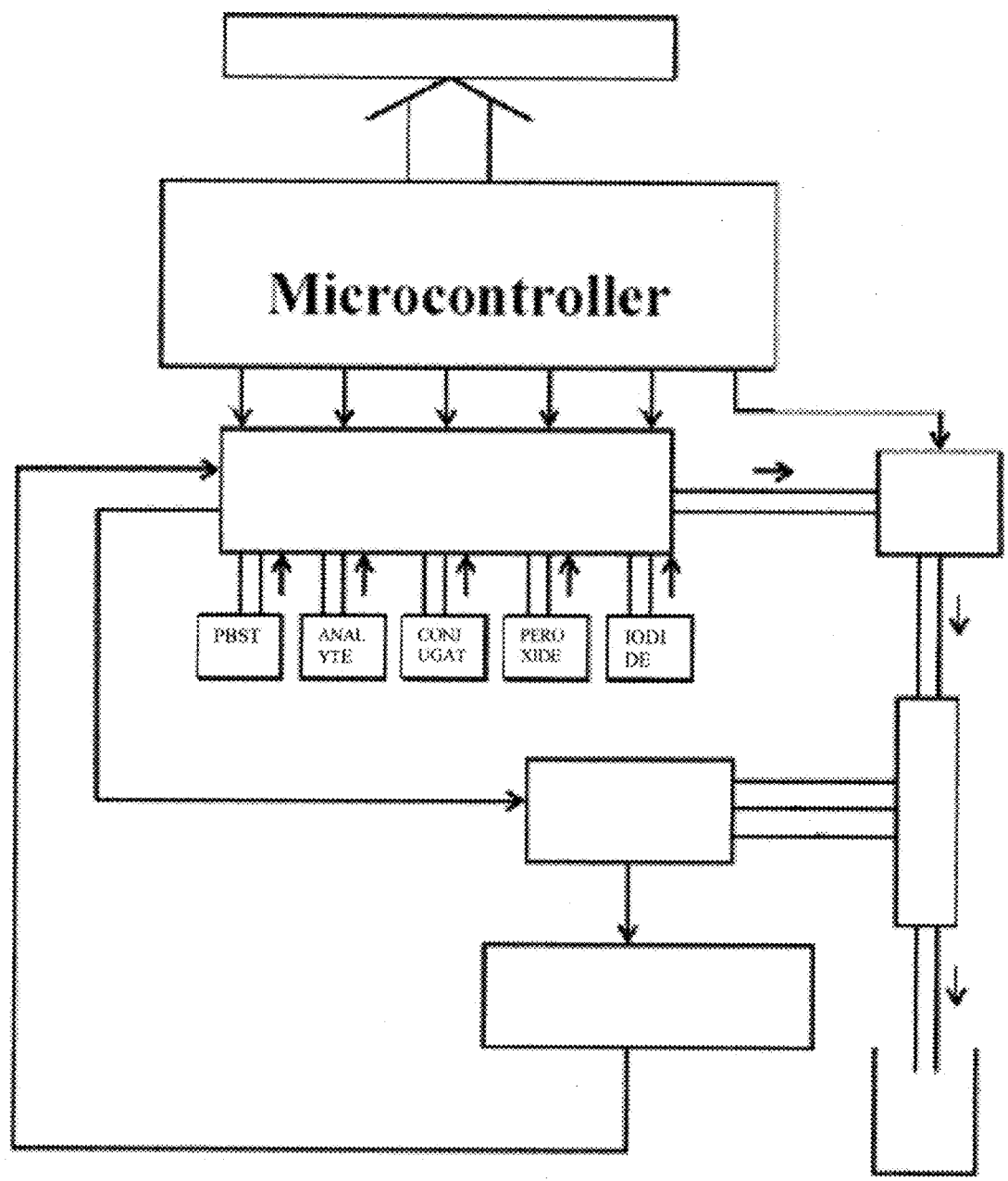
FIG. 12 Schematic layout of the immunosensor unit

The present invention further relates to an automated system of flow-through immunoassay. In a preferred embodiment, the automated system consists of four blocks: a power supply, a potentiostat, a pumping system, and a microcontroller. The power supply uses either batteries or 110 AC to generate all the voltages used in the unit. The potentiostatis used to bias the immuno-electrode and convert its current into a voltage signal. The pumping system delivers the reagents used to test the sample. And the microcontroller runs the program used to test the sample and display the results. FIG. 12 shows the schematic of the immunosensor layout.

During operation, the microcontroller switches the pump on and the fluids are pumped through the manifold valve system. The microcontroller is programmed so that it opens a particular valve during a particular stage of the assay, and a peristaltic pump pumps the required fluid through the valve. The pump speed is adjusted by adjusting the speed range pot so that a required flow rate is obtained.

The automated immunoassay system may also comprise two push-button switches and a liquid crystal display module (LCD). First button is the "start/yes" button and the second is the "no" button. When all the required fluids are filled and the electrodes are connected to the potentiostat, the assay procedure is started by pushing the "start/yes" button. The LCD displays the stages of the assay procedure. When the assay procedure is in the measuring stage, voltage is applied between the working and counter electrodes by potentiostat. The timing of application of the potential is controlled by the microcontroller. When the assay procedure is finished, the LCD displays the measurements.

Preferably, the performance of the system is evaluated before use. The first step of evaluation is to test the flow rate of the fluids through the valves. The speed range pot on the peristaltic pump is adjusted to adjust the pumping speed. The flow rate is measured by collecting fluid from the valves for a known time. The speed range pot is adjusted till the desired flow rate is obtained.

Figure 13:
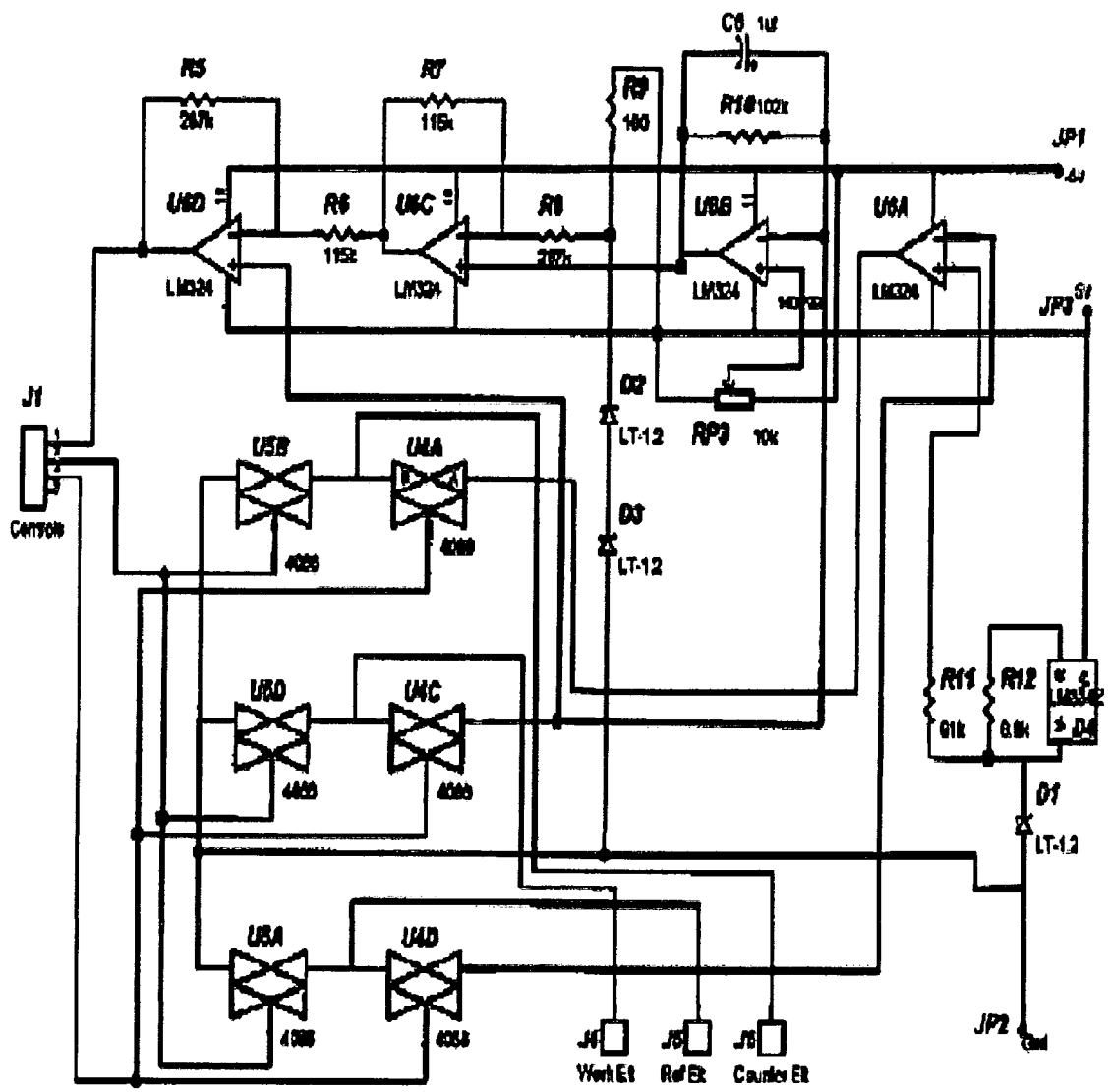
FIG. 13 Wiring Diagram, for Potentiostat
Figure 14:
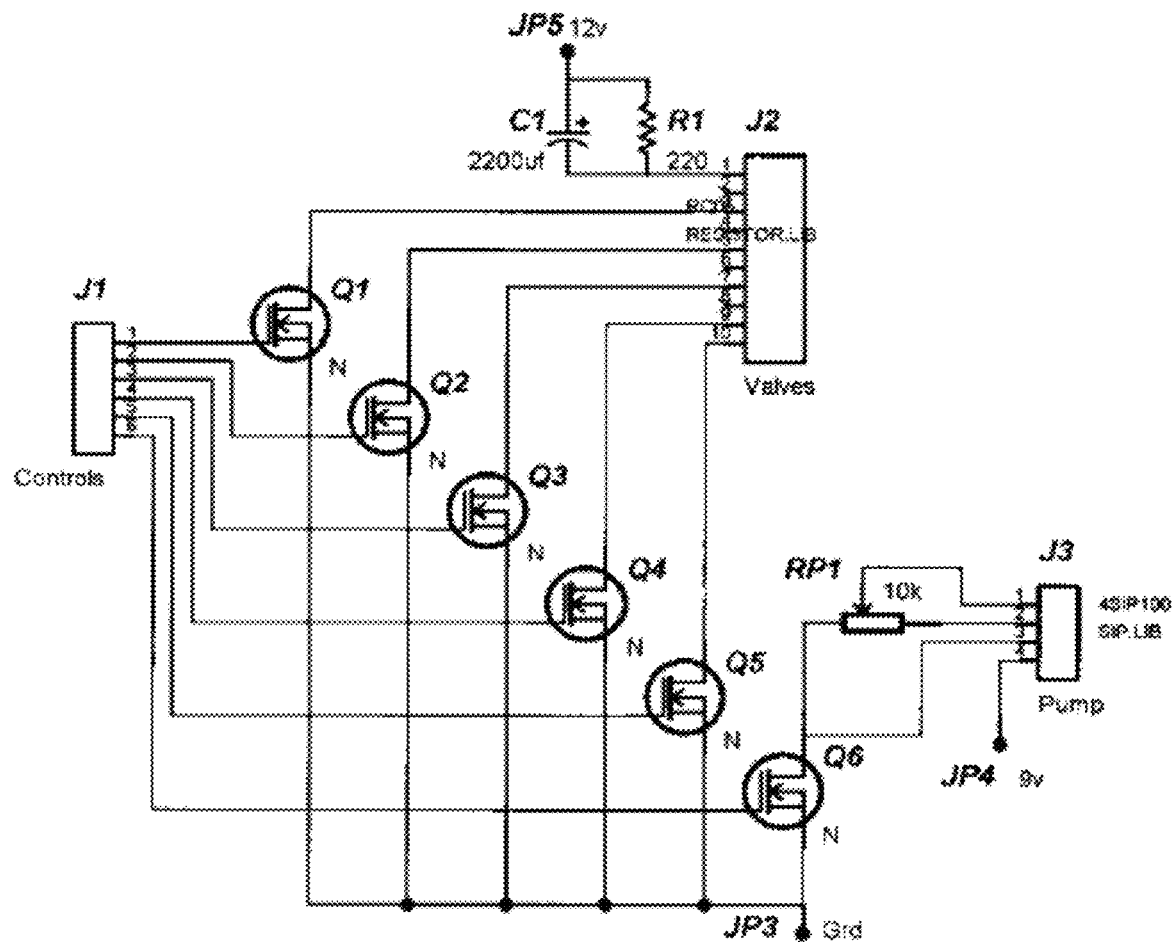
FIG. 14 Wiring diagram for the pumping system. The pumping system consists of an Instech Model P625 Peristaltic pump and HEX NC Manifold Valve Model 225T09 (Neptune Research and Development Inc., New Jersey, USA). This Manifold Valve system incorporates six separated normally-closed Teflon isolation valves integral to a single block of Teflon. The six valves had independent inlets and one common outlet. The signals that controlled these devices are 5 v digital signals, but the pump was a 9 v device and the valves were 12 v devices. So the system used MOSFETS to drive the devices from the 5 v signals.
Figure 16:
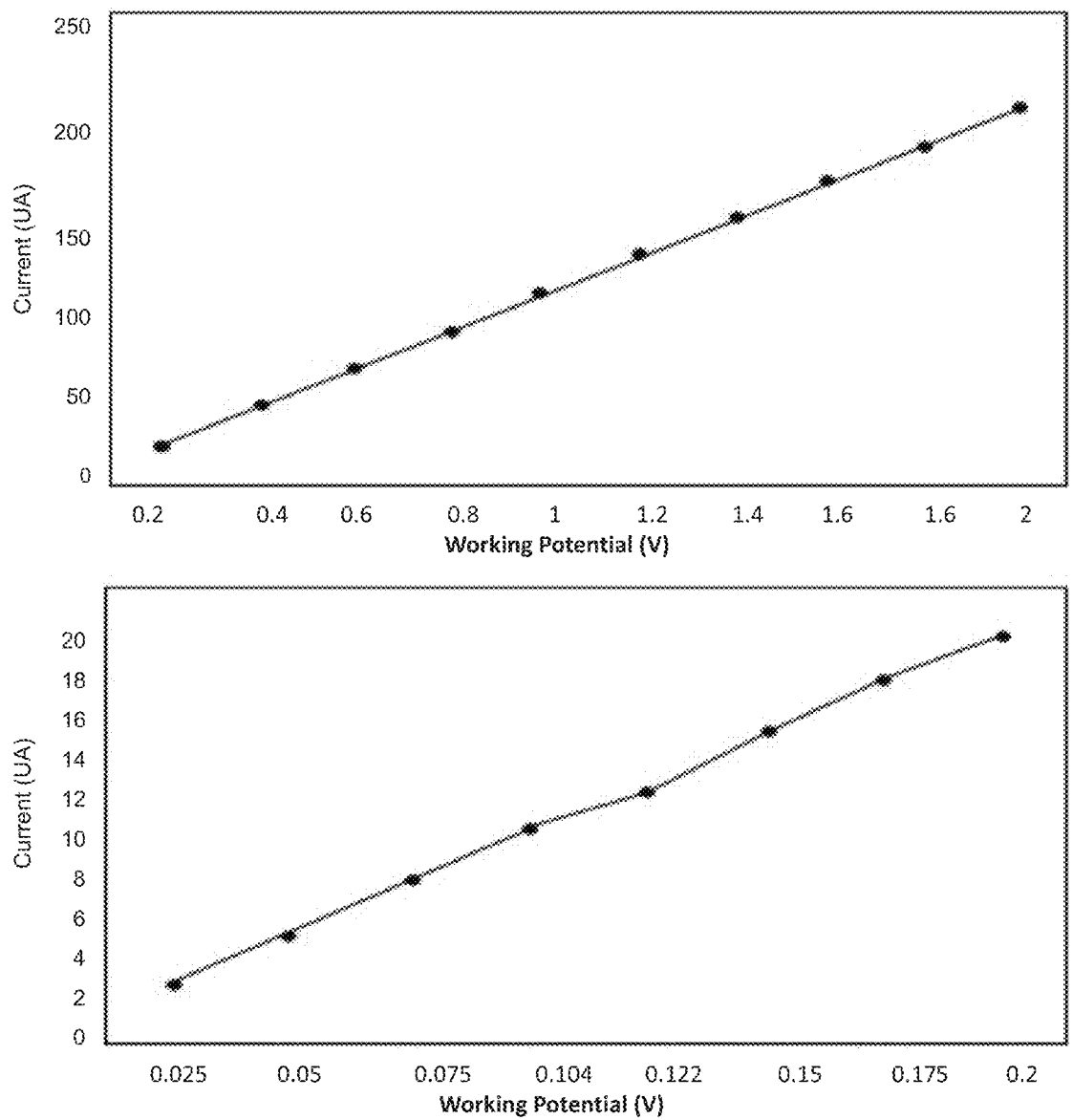
FIG. 16 Current response for various potentials for (A) a standard potentistat, (B) Potentiostat circuit in a buffer solution.

The next step is to evaluate the potentiostat circuit by connecting it to a buffer solution and applying a potential. Varying the resistance varies the potential applied and the output current is measured. Similarly a standard potentiostat is taken and various potentials are applied and the output current is noted. A graph between current and voltage is plotted. Both the results gave almost a linear dependence (FIG. 13).

Further, the resistance is adjusted so that the desired potential is applied by the potentiostat circuit. Then buffer was pumped through the valves and the buffer flowing from the valves was collected for each stage. The collected buffer was measured and the flow time of each stage was adjusted by programming the microcontroller, so that the required amount of fluid was flowing in each stage.

There are many advantages by using the automated immunoassay system as disclosed in the current invention. The assay is completely automated so that little human intervention is needed to complete an assay. Further, the assay can be stopped or started at any stage of the process. The total assay time is reduced when compared with the time required for manual assaying and the data acquisition can be connected to a computer or data storage unit for analysis or storing. Additionally, different assay procedures can be programmed into the microcontroller so that the system can be easily adapted for the detection of different pathogens.

The current invention can be better illustrated by the following examples.

Example 1

Coating Nylon Membrane with Graphite Powder

Nylon membranes were obtained From Pall Corporation, New York, N.Y. (Biodyn™ B, C, with pore sizes of 0.45, 1.2, 3.0, and 5.0 μm.) Graphite powder was obtained from Fischer Scientific, Pittsburgh, Pa., which was sieved by 53 μm mesh to obtain a particle size of 53 μm or lower.

When using the dip coating method, 1.0 g of the sieved graphite powder was mixed in 1.0 ml of cellulose acetate solutions of 25%, 50% and 75% (v/v) in acetone to form a slurry and a piece of nylon membrane (2×4 cm) was dipped in the slurry for a number of times to form layers of graphite coating. The dip-coated membranes were then dried at room temperature before use.

When coating the nylon membrane, a spin coater model no. EC101, manufactured by Headway research Inc., Garland, Tex., was used. The same above mentioned slurry was used to coat the nylon membranes. The speed of 4000 rpm was used for different amount of time (e.g. 30, 60, 90 and 120 seconds) to achieve layers with different thickness.

Membranes prepared using the spin-coating and the dip-coating methods were tested to verify conductivity and other characteristics. The resistance of graphite-coated nylon membranes prepared by both methods was about 0.38Ω. Further, as shown by the SEM photographs, the spin-coating technique produced a well controlled, thin, and evenly distributed graphite layer. The pores size produced by spin-coating was about 0.5 μm. On the other hand, graphite layers formed by dip-coating technique were less controlled and thicker, with the average pore-size is in the range of about 3 μm, which was much higher than the one produced by spin-coating.

The electrochemical properties of the graphite coated nylon membranes were further evaluated by cyclic voltammetry. As shown in FIGS. 2a and 2b, iodine reduction peaks were more pronounced in the dip-coated membranes. Furthermore, the difference in current magnitude between the CV in absence and presence of iodine was much greater in the case of dip-coated membranes. This may be attributed to the higher surface areas of graphite that is available, as shown from the SEM photographs.

The graphite coated membranes were further processed for immobilizing the desired antigen or antibody. In one embodiment of the invention, E. Coli antibodies were immobilized on the graphite coated membranes. Specifically, the membranes were first cut into one centimeter squares and placed into separate wells of a polystyrene plate. The membranes were then immersed in 1 ml of 20 mg/ml solution of Woodward's Reagent K (pH 4.5) and incubated with simultaneous shaking for 2 hours at room temperature. The membranes were washed three times (3 minutes each time) in 1 ml of 20 mM Na-phosphate buffer solution (pH 7.8). The membranes were transferred to a new polystyrene plate and left for 20 minutes to dry. Consequently, 20 μl stock solution (3 mg/ml) of anti-E. Coli antibodies were dropped onto each membrane and left at room temperature for 20 minutes to dry. The membrane was then incubated for 2 hours with 5 mg/ml of trypsin inhibitor prepared in 0.1 M phosphate buffer (pH 7.8) and stored at 4° C. until further use.

Different concentrations of E. Coli cells were added to each antibody modified membrane and incubated at 20° C. for ten minutes. The membranes were washed 3 times (3 minutes each) in 1 ml of 20 mM phosphate buffer solution (pH 7.8) to remove any unbounded E. Coli cells. Then 10 μg/ml solution of anti-E. Coli horseradish peroxidase (HRP) conjugate were added to each membrane and again incubated at 20° C. for ten minutes. The membranes were washed 3 times (3 minutes each) in PBST (pH 5.6). Each membrane was then immersed in the substrate solution (0.1 mM NaI +0.1 mM $H_2O_2$) to measure the electrochemical current at +0.105V. The set up used for the amperometric measurements is shown above.

As shown in the equations below, HRP catalyzes the oxidation of iodide into iodine. Electrochemical reduction of iodine forms the basis of determination of the activity of HRP enzyme and quantification of the enzyme label.

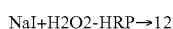

$$NaI+H2O2-HRP \rightarrow I2$$

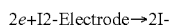

$$2e+I2\text{-Electrode} \rightarrow 2I-$$

FIG. 3 shows a calibration curve obtained for amperometric measurement of iodine using the optimized dip-coated membrane. It can be seen that concentrations as low as 0.1 mM of iodine were detected, demonstrating that the membrane has excellent sensitivity and superior electrochemical performance.

Application of the optimized membranes to the detection of E. Coli, L. monocytogenes and campylobacter C. Jejuni concentration is 40 cells/ml, is shown in FIG. 3 (a,b and c).

It was observed that the lower detection limit of total E. Coli, of L. monocytogenes, and campylobacter C. Jejuni concentration is 40 cells/ml, with a readily detectable range form 40 to 1000 cells/ml. When the E. coli concentration was greater than 1000 cells/ml, a decreased amperometric measurement was obtained, indicating a "hook effect" wherein the electrode surface was partially blocked by E. coli bacteria.

Example 2

The Detection of Hantivirus in Mice Blood Materials

Rabbit IgG, anti rabbit-IgG antibodies, peroxidase labeled Goat anti-IgG (conjugate), peroxidase labeled Goat anti-peromyscus leucopus IgG, phosphatase labeled Goat anti-peromyscus leucopus IgG were from Sigma Chemical Co. (MO, USA). Recombinant replica of Sin Nombre Virus (SNV) protein was obtained from Dr. Brian Hjelle, Department of Pathology, UNM, in kind support. Sodium phosphate (Monobasic), sodium phosphate (Dibasic), sodium acetate (Trihydrate), Sulphuric Acid were from Fisher Scientific Co. (NJ, USA). Sodium chloride, sodium hydroxide were from J T Baker. (NJ, USA). Tween 20 (Polyxyethylenesorbitan Monolaurate) was from Sigma Chemical Co. (MO, USA). ULTI (Ultra Low Temperature Isotropic Carbon) was from Carbon medics Inc. (TX, USA). Woodward's reagent K (N-ethyl-5-phenylisoxazolium-3'-sulfonate), Trypsin inhibitor, Bovine Serum Albumin, Hydrogen Peroxide (30% v/v aqueous solution), α-Naphthyl phosphate were from Sigma Chemical Co. (MO, USA). Hydrochloric acid, Sodium Hydroxide, Sodium Iodide were from J T Baker (NJ, USA).

Sensor Design

The immunoassay system design concept is based on conducting enzyme-linked assays by utilizing flow of analyte and immunochemicals through porous immunosorbents (carbon) coupled with electrochemical based transduction mechanisms as a means of overcoming the limitation associated with conventional techniques. From the engineering perspective, the use of flow-based systems allows for easier automation of the analysis procedure since pumps usually drive the flow and valves that are easily controlled by microprocessor based technology.

Preparation of Immunosorbent

Woodward's reagent K immobilization is a technique for obtaining covalent linkage of the proteins to the surface of the carbon (covalently linked immuno-reagent-solid phase conjugates). First, an activation of the solid support is performed. Second, coupling of the antibody to the activated solid support occurs. It does not leave traces of itself after the process. The pH of the solution with Woodward's reagent K (20 mg/ml) in water was adjusted to 4.5 using diluted NaOH solution, followed by suspension of 25 mg of Ultra Low Temperature Isotropic Carbon (Product of Carbon medics Inc.) in 1 mL of it. This is followed by incubation at room temperature for 2 hours with shaking. The suspension was later washed 5 times with distilled water by repeated centrifugation and removal of the supernatant. Carbon thus treated with Woodward's reagent K was suspended in 1 mL of a solution of IgG (0.5 mg/mL). The suspension was incubated at room temperature for 2 hours with shaking. After incubation, the carbon particles are again washed for five times with distilled water with repeated centrifugation and removal of the supernatant. 5 mg of trypsin inhibitor is then added to the same suspension as a blocking agent and incubated for an additional 2 hours at room temperature with shaking. The suspension was finally washed 5 times with PBS by repeated centrifugation (5 minutes each) and removal of the supernatant. The immuno-sorbent was stored in the same buffer solution at 4° C. The immobilization of recombinant nucleocapsid Hantavirus protein antibodies (10 μg/mL) is performed similarly.

The System

The power supply system used DC-to-DC converters to generate the +12 V, +9 V, +5 V, and −5 V signals needed by the other systems. A pair of 9 V batteries was used for portable power, but a relay will disconnect the batteries if a 12 V power pack was plugged into the external jack.

An AT89C51, 8-bit microcontroller was used, which was a low-power, high-performance CMOS microcomputer with 4K bytes flash programmable and erasable read only memory (PEROM). The microcontroller was the heart of the system and controlled the functioning of all the electronic parts in the system. The micro controller system used an 8051 chip to run the test program for the unit. It generated the control signals for the pumping system, used an analog to digital converter to acquire data from the potentiostat, and displayed the results on an LCD display.

The potentiostat used a constant current source to supply the biasing of the immunoelectrode, and instrumentation amplifiers to convert the electrode current into a voltage signal. The system also used digital switches to ground the electrode when it isn't being used. The required potential between the working and the counter electrode was applied and the output signal i.e., the current between the working and the reference electrode was measured by the potentiostat.

The pumping system consists of an Instech Model P625 Peristaltic pump and HEX NC Manifold Valve Model 225T09 (Neptune Research and Development Inc., New Jersey, USA). This Manifold Valve system incorporates six separated normally-closed Teflon isolation valves integral to a single block of Teflon. The six valves had independent inlets and one common outlet. The signals that controlled these units are 5 v digital signals, but the pump was a 9 v unit and the valves were 12 v units. So the system used MOSFETS to drive the units from the 5 v signals.

The hantavirus assay had six stages of pumping. The first stage, the microcontroller was programmed to pump 0.02 M Na-phosphate buffer (pH 7.8) containing 0.15 M NaCl and 0.1% Tween-20 (PBST) for 1 minute through valve 1. This was a pre-washing stage, wherein the immuno-sorbent was washed with the PBST. The second stage was sample injection stage where the microcontroller pumped PBST containing blood samples, tested for Hantavirus IgG antibodies (target analyte) through valve 2, for 3 min. In this stage the target analyte was bound to the surface of the immunoelectrode. Stage three was washing stage where the microcontroller was programmed to open valve one and pump PBST for 2 minutes. In stage four the conjugate was injected. The microcontroller opened valve 3 and pumped 2 ug/ml of peroxidase-labeled anti-human IgG (conjugate) against the target analyte flow through the immunocolumn for 8.5 min. Stage five was again a washing stage where 0.05 M Na-bicarbonate buffer solution (pH 9.6), containing 0.01 M NaOH and 0.15 M NaCl was pumped through valve 4 for 4 min by the microcontroller. In the final stage, the microcontroller pumped 0.05 M Na-bicarbonate buffer solution (pH 9.6), containing 0.01 M NaOH and 0.15 M NaCl, 0.1 mM α-Naphthyl phosphate, flow through the valve 5 for 5 min. The amperometric measurements were performed at a fixed electrode potential (+105 mV vs. Ag/AgCl) which was applied by the potentiostat.

Methodology

Highly dispersed carbon or carbon filter paper offers a large surface area and at the same time functions as the working electrode because of its conductive nature or it can work without being the electrode. The material possesses characteristic area per unit mass and the particle sizes lie in the same order of magnitude as that of proteins. This provides the basis for immobilization of antibodies on this carbon. Such a process enhances the proximity of biological components with the transducer, a very essential factor for biosensor development. ULTI is used as a material for the working electrode in a finely dispersed powder form (fraction less than 275 mesh size of an ASTM sieve). Current collection is achieved through a carbon rod, while the reference Ag/AgCl and carbon represent the reference electrode and the counter electrode respectively. Amperometry is a technique where the output of the sensor is current, which is measured by applying a constant potential between the working and reference electrodes. The signal is due to electrochemical process involving the analyte, taking place at the electrode surface. The potential difference is termed working potential and is determined by cyclic voltammetry.

The ULTI immunosorbent/filter carbon modified by immobilized recombinant replica of Hantavirus envelope was used for "sandwich immunoassay" of Hantavirus detection. ULTI carbon, containing immobilized antibodies, was deposited in the disposable sensing element as shown in by centrifugation. The small size of carbon particles increases the rate of immunointeraction at each stage. Horseradish peroxidase (HRP) attached as a label to the anti-human IgG catalyses the oxidation of iodide into iodine. Electrochemical reduction of iodine forms the basis for determination of the activity of HRP enzyme and quantification of the enzyme label. The scheme of reaction is as follows:

$$2I^- + H_2O_2 + 2H^+ \rightarrow I_2 + 2H_2O \quad \text{Equation 1}$$

$$I_2 + 2e \rightarrow 2I^- \quad \text{Equation 2}$$

The amount of iodine formed by reaction Equation 1, detected using reaction Equation 2, is a measure of the activity of HRP label. Since the amount of antigen (analyte) determines the amount of HRP-labeled antibodies that bind to form the sandwich, amperometric measurement of iodine formed is directly proportional to the analyte concentration. The sandwich complex replaced by alkaline phosphatase labeled immunoconjugate (AP) where HRP was previously used, where the hydrolysis of α-Naphthyl Phosphate to α-Naphthol is determined amperometrically.

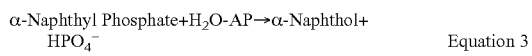

$$\alpha\text{-Naphthyl Phosphate}+H_2O\text{-AP}\rightarrow\alpha\text{-Naphthol}+HPO_4^- \quad \text{Equation 3}$$

Results

The assay procedure described above was used initially to test the response of the system using rabbit IgG as the analyte. The rabbit IgG is immobilized on the immunosorbent and anti-rabbit IgG is used as antibody. Both peroxidase labeled and alkaline phosphatase labeled anti-rabbit IgG were used separately. FIG. 15. Tables 1 and 2 show the response of the system using these conjugates.

The data for both the type of the conjugates indicate the data is reproducible. But the alkaline phosphatase labeled conjugate gave higher current than peroxidase labeled conjugate. This implies that the reaction of α-Naphthyl Phosphate to α-Naphthol yields higher current than the reduction of iodine to iodide. Hence further experiments were done using alkaline phosphatase labeled conjugate.

Mice blood samples were then tested by the same assay procedure. The recombinant replica of Sin Nombre Virus (SNV) protein was immobilized on the immunosorbent. Phosphatase labeled Goat anti-peromyscus leucopus IgG was used as the conjugate. The table below gives the results obtained from the unit and that from genomic determination. See FIG. 15 Table 3.

The next step was to evaluate the potentiostat circuit. To do this the electrode system was connected to the potentiostat circuit and potential was applied on a buffer solution. Varying the resistance varied the potential applied and the output current was measured. Similarly a standard potentiostat was taken and various potentials were applied and the output current was noted. A graph between current and voltage was plotted in FIG. 16. Both the results gave almost a linear dependence.

Taking a negative blood sample and diluting it to very low concentrations, the negative control current was obtained. Similarly a positive control was obtained by diluting positive sample to low concentrations. Hence if the response current is above the positive control it can be said that the given sample is positive for Hantavirus antibodies. If the response is below that of the negative control current it can be said that the sample is negative. If the response lies between these values, the sample cannot be determined.

No false positive or false negative was obtained.

CONCLUSION

The potential of the portable amperometric immunosensor based on a recombinant nucleocapsid antigen and highly dispersed flow immunoelectrode for fast determination of hantavirus infection in mice blood serum under field conditions has been demonstrated. The system design is based on an amperometric immunosensor that employs disposable sensing elements. This approach combines the advantages of utilization of highly dispersed immunosorbent, flow-through scheme of immunoassay and, highly sensitive electrochemical determination of enzyme label. A main benefit of recombinant nucleocapsid antigen application in immunoassay is that antigen preparation is easy to standardize. Since the principle of disposable sensing elements is involved, no regeneration of immunosorbent between measurements is required.

The potential of the portable amperometric immunosensor based on total *E. Coli, L. monocytogenes*, and *campylobacter C. Jejuni* as antigen and highly dispersed flow immunoelectrode for fast determination of the above infection in blood serum, drinks, food, saliva or urine under field conditions has been demonstrated. The system design is based on an amperometric immunosensor that employs disposable sensing elements. This approach combines the advantages of utilization of highly dispersed or a filter of immunosorbent, flow-through scheme of immunoassay and, highly sensitive electrochemical determination of enzyme label. A main benefit of total *E. Coli*, of *L. monocytogenes*, and *campylobacter C. Jejuni* concentration or recombinant nucleocapsid antigen application in immunoassay is that antigen preparation is easy to standardize. Since the principle of disposable sensing elements is involved, no regeneration of immunosorbent between measurements.

The format of the assay and its proven applicability make it suitable for standardized used at field located at remote sites, with minimal technical expertise. The handy immunosensor can be used to discrete the samples (positive and negative) without any pretreatment of the samples in a well-defined time interval (25 minutes). The unit is extremely useful for studies relating to population screening of hantavirus in mice or human blood in remote areas with limited facilities, to simplify blood collection and reduce costs without unduly sacrificing analytical accuracy. The unit can be easily adapted for fast analysis of other microorganisms in biological, physiological and analytical practices under non-laboratory conditions and field operations such as bacteria, DNA and parasites.

What claimed is:

1. A flow-through immuno-sensor with electrochemical detection capabilities, comprising:

a body;

an electrode assembly housed within the body, the electrode assembly comprising a first substrate supporting a working electrode a second substrate supporting a reference electrode and a counter electrode:

a detector configured to detect an electrical signal generated by the working electrode; wherein the body also has a fluid inlet configured to introduce a fluid sample into the body; a fluid path in communication with the fluid inlet, the fluid path being configured to allow fluid to encounter the working electrode, the counter electrode, and the reference electrode; and an outlet channel;

wherein the working electrode comprises immobilized antibody or antigen and is configured for an enzyme reaction so forming a reaction region; and wherein when test sample comprising a target analyte antibody or antigen is introduced to the reaction region via the inlet channel under sufficient conditions for the target analyte to bind to the immobilized antibody or antigen, unbound molecules in test sample exit the reaction region via the outlet channel, and thereafter when one or more detection molecules are introduced to the reaction region an enzymatic reaction will occur, the product of which is able to produce a detectable alteration in the working electrode's signal output.

2. The flow-through immuno-sensor with electrochemical detection capabilities of claim 1, further comprising an immuno-selective membrane in fluidic communication with the fluid inlet and the working electrode.

3. The flow-through immuno-sensor with electrochemical detection capabilities of claim 1, wherein the working electrode is screen-printed on the first substrate.

4. The flow-through immuno-sensor with electrochemical detection capabilities of claim 1 wherein the antibody or antigen enables physical contact between the target analyte and the working electrode.

5. The flow-through immuno-sensor with electrochemical detection capabilities of claim 4 wherein the test sample is selected from the group consisting of blood, body fluid, animal fluid, environmental sample, and warfare agent.

6. The flow-through immuno-sensor with electrochemical detection capabilities of claim 4 wherein the working electrode comprises a coating of electro-conductive layer including conductive particles, wherein the conductive particles are carbon particles, graphite, or ULTI immuno-sorbent; and wherein the coating further comprises a multi analyte-specific antibody or antigen.

7. The flow-through immuno-sensor with electrochemical detection capabilities of claim 1 wherein the working electrode comprises multi micro-channels and wherein the micro-channels are fluidly connected to the fluid inlet such that the fluid sample flows through the channels.

8. A multi-channel flow-through sensor with electrochemical detection capabilities, comprising: a substantially planar body; multiple fluid channels connected to the body, each fluid channel in fluidic communication with an electrode assembly, each electrode assembly comprising a substrate and a working electrode, along with a fluid inlet configured to introduce a fluid sample into the body from a fluid channel and to present a target analyte in the fluid sample to the working electrode such that an electrical signal generated by the working electrode is altered; and a detector configured to detect the electrical signal generated by the working electrode: wherein antibody or antigen is immobilized on the carbon particles deposited on top of the working electrode that enables physical contact between the target analyte and the working electrode.

9. A multi-channel flow-through sensor with electrochemical detection capabilities the sensor of claim 8 wherein the antibody or antigen produces a chemical reaction when exposed to the target analyte and the product of the chemical reaction alters the electrical signal generated by the working electrode.

* * * * *